US011788040B2

(12) United States Patent
Asalapuram et al.

(10) Patent No.: US 11,788,040 B2
(45) Date of Patent: Oct. 17, 2023

(54) DIAGNOSTIC DEVICE AND RELATED METHOD

(71) Applicant: EMPE Diagnostics AB, Solna (SE)

(72) Inventors: Pavankumar Asalapuram, Huddinge (SE); Mats Nilsson Bernitz, Drottningholm (SE)

(73) Assignee: EMPE DIAGNOSTICS AB, Solna (SE)

( * ) Notice: Subject to any disclaimer, the term of this patent is extended or adjusted under 35 U.S.C. 154(b) by 241 days.

(21) Appl. No.: 16/076,672

(22) PCT Filed: Feb. 15, 2017

(86) PCT No.: PCT/SE2017/050147
§ 371 (c)(1),
(2) Date: Aug. 8, 2018

(87) PCT Pub. No.: WO2017/142467
PCT Pub. Date: Aug. 24, 2017

(65) Prior Publication Data

US 2019/0048304 A1 Feb. 14, 2019

(30) Foreign Application Priority Data

Feb. 15, 2016 (SE) .................................... 1650197-5

(51) Int. Cl.
*C12M 1/34* (2006.01)
*C12M 1/12* (2006.01)
(Continued)

(52) U.S. Cl.
CPC ............ *C12M 1/34* (2013.01); *B01L 3/5023* (2013.01); *C12M 23/04* (2013.01); *C12Q 1/68* (2013.01);
(Continued)

(58) Field of Classification Search
CPC ..... B01L 2200/0647; B01L 2300/0816; B01L 2300/0825; B01L 2300/0864;
(Continued)

(56) References Cited

U.S. PATENT DOCUMENTS 5,169,787 A 12/1992 Knappe et al.
2002/0025576 A1 2/2002 Northrup et al.
(Continued)

FOREIGN PATENT DOCUMENTS

EP 0634215 A1 1/1995
WO WO 03/008971 1/2003
(Continued)

OTHER PUBLICATIONS

Pavankumar et al., "Detection of isoniazid-resistant *Mycobacterium tuberculosis* by padlock probes combined with lateral flow nucleic acid biosensor", 2014, Conference paper, 35th Annual Congress of the European Society of Mycobacteriology & Poster downloaded from https://f1000research.com/posters/1096372.
(Continued)

*Primary Examiner* — Lydia Edwards
(74) *Attorney, Agent, or Firm* — James S. Keddie; Bozicevic, Field & Francis LLP

(57) ABSTRACT

The present invention relates to a device (10; 30; 50) for analysing liquid samples comprising amplified nucleic acids, said device comprising: a sample pad (16); a first (18) and a second (19) sample analysis strip configured to analyse different aspects of the nucleic acid sample wherein said segments comprise nucleic acid sequences which are complementary to the predetermined sequences of target nucleic acids whose presence or absence is analysed; and a housing (11) enclosing said sample pad and at least two elongated sample analysis strips wherein the analysis result is detectable from the outside of the housing from the combination of aligned segments of said first and second analysis strips. The invention furthermore relates to a method for determining the presence or absence of a target nucleic acid, providing confirmatory results, in combination with a predetermined sequence in a sample from a subject using the device according to the invention.

18 Claims, 9 Drawing Sheets

(51) Int. Cl.

*B01L 3/00* (2006.01)
*C12Q 1/689* (2018.01)
*C12Q 1/68* (2018.01)
*C12Q 1/6806* (2018.01)
*C12Q 1/686* (2018.01)
*C12Q 1/6869* (2018.01)

(52) U.S. Cl.

CPC ...... *C12Q 1/689* (2013.01); *B01L 2200/0647* (2013.01); *B01L 2300/0816* (2013.01); *B01L 2300/0825* (2013.01); *B01L 2300/0864* (2013.01); *B01L 2400/0406* (2013.01); *B01L 2400/0457* (2013.01); *C12Q 1/6806* (2013.01); *C12Q 1/686* (2013.01); *C12Q 1/6869* (2013.01)

(58) Field of Classification Search

CPC ..... B01L 2400/0406; B01L 2400/0457; B01L 3/5023; C12M 1/34; C12M 23/04; C12Q 1/68; C12Q 1/6806; C12Q 1/686; C12Q 1/6869; C12Q 1/689

See application file for complete search history.

(56) References Cited

U.S. PATENT DOCUMENTS

2008/0317633 A1 12/2008 Sibbett et al.
2015/0056687 A1* 2/2015 Tyrrell .................. B01L 3/5023 435/287.2

FOREIGN PATENT DOCUMENTS

WO WO 2010/079479 7/2010
WO WO 2013/163353 10/2013
WO WO 2015/033229 3/2015

OTHER PUBLICATIONS

Yetisen et al., "Paper-based microfluidic point-of-care diagnostic devices", 2013, 13: 2210-2251.
Lacoma et al., "GenoType MTBDRplus Assay for Molecular Detection of Rifampin and Isoniazid Resistance in *Mycobacterium tuberculosis* Strains and Clinical Samples", Journal of Clinical Microbiology, 2008, 46(11): 3660-3667.
Fenton et al., "Multiplex Lateral-Flow Test Strips Fabricated by Two-Demensional Shaping", ACS Applied Materials & Interfaces, 2009, 1(1): 124-129.
Pavankumar et al., "Proficient Detection of Multi-Drug-Resistant *Mycobacterium tuberculosis* by Padlock Probes and Lateral Flow Nucleic Acid Biosensors", Anal Chem., 2016, 88: 4277-4284.
Kamphee et al., "Rapid Molecular Detection of Multidrug-Resistant Tuberculosis by PCR-Nucleic Acid Lateral Flow mmunoassay", Plos ONE, 2015, 10: e0137791.
Kaewphinit et al., "Detection of *Mycobacterium tuberculosis* by using loop-mediated isothermal amplification combined with lateral flow dipstick biosensor", The 2011 Biomedical Engineering International Conference, (BMEICON-2011), 2011, pp. 86-88.
Niemz et al., "Point-of-care nucleic acid testing for infectious diseases", Trends in Biotechnology, 2011, 29(5): 240-250.
Lu et al., "System for Portable Nucleic Acid Testing in Low Resource Settings", Proceeding of SPIE, 2013, vol. 8615.
Zhang et al., "A novel genotypic test for rapid detection of multidrug-resistant *Mycobacterium tuberculosis* isolates by a multiplex probe array", Journal of Applied Microbiology, 2007, 103(4): 1262-1271.

* cited by examiner

Figure 4A

| SEQ ID NO | Oligo ID | Name | Sequence (5' --> 3') | Description | 5' modification | 3' modification |
|---|---|---|---|---|---|---|
| 1 | S01233 | *rpoB* 531 wt Atag- | AAAAAAAAAAAAAAAGATCACACTTACGGAACAGC | Strip oligonucleotide | Biotin | |
| 2 | S01234 | *rpoB* 531 TTG Atag- | AAAAAAAAAAAAAAAGATCTAACGCACGGGAACTC | Strip oligonucleotide | Biotin | |
| 3 | S01237 | *katG* 315 wt Atag- | AAAAAAAAAAAAAAACTGAGAGTTCGATGACCTGT | Strip oligonucleotide | Biotin | |
| 4 | S01239 | *katG* 315 ACC Atag- | AAAAAAAAAAAAAAAAATGCTCGGGAAGGCTACTC | Strip oligonucleotide | Biotin | |
| 5 | S01235 | TB-control oligo_v1 | ATAGTGTCTTACTTAAAAAAAAAA | Strip oligonucleotide | | Biotin |
| 6 | S01236 | TB-Gold Oligo_v1 | GTAAGACACTATTACTGAGGAGAAAAAAAAAA | AuNP-oligonucleotide conjugate | | Thiol |
| 7 | S00448 | *katG* 315 wt | TGGTGATCGCGTCCTTACCACAGGTCATCGAACTCTC AGGTGTATGCAGCTCCTCAGTAATAGTGTCTTACATA CGACCTCGATGCCGC | Padlock probe | | |
| 8 | S00565 | *katG* 315 ACC | TGGTGATCGCGTCCTTACCGAGTAGCCTTCCCGAGCA TTGTGTATGCAGCTCCTCAGTAATAGTGTCTTACATA CGACCTCGATGCCGG | Padlock probe | | |
| 9 | S00592 | *rpoB* 531 wt RS Popeye2 | GGCGCTGGGGTTGCTGTTCCGTAAGTGTGATCGTGT ATGCAGCTCCTCAGTAATAGTGTCTTACTGGTTGACC CACAAGTTTTTCCGACTGTC | Padlock probe | | |
| 10 | S00228 | *rpoB* 531 TTG RS v1 | GGCGCTGGGGGAGTTCCCGTGCGTTAGATCGTGTAT GCAGCTCCTCAGTAATAGTGTCTTACGCGCCGACTGT T | Padlock probe | | |
| 11 | L11783 | TB *rpoB* CO RS | CTCTCTCTCTCTCTCTCTCTCTGTCCGCGACGTGCACCCG TCGCACTACGGCCGGATGTGCC | Capture oligonucleotide | Biotin | |
| 12 | L11860 | *katG* CO | CTCTCTCTCTCTCTCTCTCTTTCCAGCCCAAGCCCATCT GCTCCAGCGGAGCAGCCTCGGGTTC | Capture oligonucleotide | Biotin | |

Figure 4B

| SEQ ID NO | Oligo ID | Name | Sequence (5' --> 3') | Description | 5' modification | 3' modification |
|---|---|---|---|---|---|---|
| 13 | S00244 | BNL_RO_*AluI* | GTGTATGCAGCTCCTCAGTA | Restriction oligonucleotide | | |
| 14 | S00166 | *AluI* RO | TACTGAGGAGCTGCATACAC | Restriction oligonucleotide | | |
| 15 | L12879 | TB *rpoB* SW RS wt v2 | GGCACATCCGGCCGTAGTGCGACGGGTGCACGTCGCGGACCCTCACGTGACAGACCGCCGGGCCCCAGCGCCGACAGTCGGCGCTTGTGGGTCAACCCCGACAGCGG | Synthetic target | | |
| 16 | L11801 | TB *rpoB* SW RS mut | GGCACATCCGGCCGTAGTGCGACGGGTGCACGTCGCGGACCTCCAGCCCGGCACGCTCACGTGACAGACCGCCGGGCCCCAGCGCCAACAGTCGGCGCTTGTGGGTCAACCCCGACAGCGGGTTGTT | Synthetic target | | |
| 17 | L12721 | *katG* SW wt v2 | GAACCCGAGGCTGCTCCGCTGGAGCAGATGGGCTTGGGCTGGAAGAGCTCGTATGGTAAGGACGCGATCACCAGCGGCATCGAGGTCGTATG | Synthetic target | | |
| 18 | L12560 | *katG* 315 ACC target | GAACCCGAGGCTGCTCCGCTGGAGCAGATGGGCTTGGGCTGGAAGAGCTCGTATGGCACCGGAACCGGTAAGGACGCGATCACCACCGGCATCGAGGTCGTATGGAC | Synthetic target | | |

DIAGNOSTIC DEVICE AND RELATED METHOD

CROSS-REFERENCE TO RELATED APPLICATIONS

This application is a § 371 national phase of International Application No. PCT/SE2017/050147, filed on Feb. 15, 2017, which claims the benefit of Swedish Patent Application No. 1650197-5, filed on Feb. 15, 2016, which applications are incorporated by reference herein.

FIELD OF THE INVENTION

The present disclosure relates to a device for analysing liquid samples, and a diagnostic method employing said device.

BACKGROUND

Infectious diseases are responsible for more than 56 million deaths yearly (>153 000 per day), where the remaining billions of affected people suffer from post-infectious morbidity conditions like malnutrition, poor mental and physical growth, impaired cognitive development, etc. Prevalent infections like diarrhea, HIV, and Tuberculosis (TB) contribute more than half of the total mortality rates and require immediate medical attention. According to the World Health Organization (WHO) and UNICEF, about 2 billion people suffer diarrhoeic diseases and 1.9 million children younger than 5 years of age die every year. This amounts to 18% of all childhood deaths (>5000 deaths per day). In 2014, about 36.9 million people were reported with HIV, where 2.6 million are children. Although the mortality rates are minimal in developed countries, about 50-80% are reported from developing countries in African and South-East Asian regions, where people lack good health care facilities and proper infectious disease diagnostics.

As an example, TB affects more than 9 million people causing 1.5 million deaths per year. The causative agent of TB, *Mycobacterium tuberculosis* (MTB), generally develops resistance by acquisition of sequential mutations in the chromosome. The mutated MTB strains become resistant to at least the two major first line anti-TB drugs, isoniazid (INH) and rifampicin (RIF), are classified as multidrug-resistant TB (MDR-TB). Further mutations in MTB contribute to extensive drug-resistance (XDR-TB) to most of the remaining antibiotics, which present a challenge for diagnosis and treatment. Primarily, MTB is detected by smear microscopy but this technique cannot identify drug-resistant strains. Culture-based drug susceptibly testing (DST) methods are laborious and time-consuming (weeks to months to obtain correct results) due to the slow growth of MTB. In contrast, polymerase chain reaction (PCR) based nucleic acid amplification tests (NAAT) provide rapid results for the detection of drug-resistant MTB strains through various automated and semi-automated techniques. For example, the real-time PCR based GeneXpert MTB/RIF (Cepheid, Sunnyvale, Calif., USA) assay provides results in less than 2 h by directly analyzing the sputum samples. The GeneType MTBDRplus probe-hybridization assay (Hain Lifescience GmbH, Nehren, Germany) is capable of detecting multiple resistance markers in parallel, but the system is estimated to detect only 95% and 74% of RIF and INH resistant strains, respectively. Additionally, these two tests are difficult to perform at resource-limited laboratories because of the requirement of trained laboratory personnel and infrastructure. Thus, the capacity and requirement for instrumentation and skilled personnel of currently available nucleic acid amplification tests (NAATs) hinder prompt detection of MDR-TB in resource-limited settings.

Correct and robust identification of disease causing microbes and their genetic pattern causing drug-resistance remains a challenge, especially in peripheral clinical set-ups. Thus, there is a continued need for improved diagnostic devices and methods in the field of diagnostics of various bacterial infections. In particular, there is a need for a simple and reliable device that could be used in combination with a proficient molecular method that can address the technical as well as clinical detection challenges of bacterial infections, for example of MDR-TB, to offer a suitable solution for peripheral resource-limited health care settings.

Examples of different types of device intended for testing samples are disclosed in WO2010/079479 and WO2013/163353 that can provide one signal from one sample target, in sequential manner. However, these results are semi-qualitative and may not provide confirmatory answers, especially impacting the antibiotic treatment. Therefore, there is a need for better and user-friendly devices enabling multiple results for a sample and provide confirmatory test results to initiate appropriate treatment, even from the first clinical contact.

SUMMARY OF THE INVENTION

It is an object of the present disclosure to provide a new device for analysing liquid samples comprising amplified nucleic acids.

It is an object of the present disclosure to provide a device that overcomes the drawbacks known from the prior art.

It is an object of the present disclosure to provide a device which enables simultaneous detection of multiple predetermined nucleic acid sequences.

It is an object of the present disclosure to provide a device which is simple, convenient to use and delivers a reliable result.

It is furthermore an object of the present disclosure to provide a device which is suitable of peripheral and resource-limited laboratory settings.

It is also an object of the present disclosure to provide a combinatorial method for the detection of multiple predetermined nucleic acid sequences.

It is also an object of the present disclosure to provide a method for the detection of the presence drug and/or antibiotic resistance bacteria, targeting gene mutations in a subject.

These and other objects, which are evident to the skilled person from the present disclosure, are met by different aspects of the invention as claimed in the appended claims and as generally disclosed herein.

Thus, in the first aspect of the present disclosure there is provided a device for analysing liquid samples comprising amplified nucleic acids, said device comprising:

- a sample pad;
- a first and a second sample analysis strip configured to analyse different aspects of the nucleic acid sample, wherein the first and second strips are elongated and extend from the sample pad and each of said first and second strips comprises a substantially straight analysis section divided into a number of segments, each configured to indicate if a target nucleic acid with a predetermined sequence is present in or absent from said sample, which target nucleic acid with a predetermined sequence is directly or indirectly coupled to a detection molecule, and wherein the analysis sections of said first and second sample analysis strips comprises a backing film covered by a transparent layer with a thickness of at least 0.1 mm, said analysis sections are configured to analyse the presence or absence of nucleic acids with different predetermined sequences, said analysis sections of the first and second sample analysis strips having substantially the same length and being arranged side by side such that the analysis result is detectable from the combination of three-dimensional marks appearing in the transparent layer of aligned segments of said first and second analysis strips, wherein said segments comprise nucleic acid sequences which are complementary to the predetermined sequences of target nucleic acids whose presence or absence is analysed; and a housing enclosing said sample pad and at least two elongated sample analysis strips, said housing comprising a front side in which a sample inlet passage is formed such that the sample pad is accessible from the outside of the housing and at least one opening such that the analysis result is detectable from the outside of the housing.

The device of present disclosure may for example make use of lateral flow nucleic acid biosensors (LFNAB). In a LFNAB, the tags comprising a nucleic acid sequence that is complementary to the predetermined nucleic acid sequence are immobilized on a membrane, for example a nitrocellulose membrane or a nylon membrane. As sample passes over the analysis strip, nucleic acid molecules comprising the predetermined nucleic acid sequence will bind to their complementary immobilized sequences.

The device according to the invention makes it possible to analyze samples without requiring further advanced medical analysis equipment which makes it very useful in geographical areas where the access to medical analysis equipment is limited. The device, due to its characteristic design, provides a detailed result facilitates correct and effective medication, avoiding empirical treatment. Therefore, it is very advantageous for the patient, and helps to avoid unnecessary adverse effects and reduces the amount of medications prescribed without treating the patient. The sample pad and analysis sections are protected by the housing and ready for use without requiring any preparations.

In particular, the device of the present disclosure provides a way of providing information about for example the drug-susceptibility pattern at the early stages of diagnosis, which could certainly help clinicians to start appropriate treatment of infectious diseases. Additionally, the present device is suitable for use in peripheral laboratory settings.

Furthermore, the different segments of the analysis sections comprising a backing film covered by a transparent layer generates a very distinct three-dimensional mark appearing in the transparent layer of the indicating segment that facilitates the reading of the result and ensures that the result is read correctly.

As used herein, the term "infectious diseases" refers to physiological illness caused by microorganisms, such as bacteria, viruses, parasites or fungi. Infectious diseases can spread, directly or indirectly, between or among humans and animals.

As used herein, the term "nucleic acids" refers to any form of deoxyribonucleic acid (DNA), which is composed of bases like adenine, guanine, cytosine, and thymine that carries genetic codes and determines biological role of any living organism. Similar to DNA but more versatile ribonucleic acids (RNA) that are formed by adenine, guanine, cytosine, and uracil transfers genetic codes and transmits the information. Therefore, the term nucleic acids refer to any form of DNA or RNA and their associates. Non limiting examples of such associates include cDNA, mRNA, tRNA, rRNA, snRNA, miRNA, si RNA, piRNa, rnRNA, scaRNA, long ncRNA, extracellular DNA and extracellular RNA.

As used herein, the term "peripheral laboratory settings" refers to any clinical laboratory, for example rural health care centers and medical camps, with very limited medical facilities, for example lacking standard equipment, dressings and drugs, antibiotics, as well as having limited or even lacking of health care personnel trained to provide diagnosis and treatment.

In one embodiment of the device as disclosed herein, the first and second sample analysis section are configured to analyse if the liquid sample comprises a wild type variant of gene or partial gene, or if it comprises a mutant variant of said gene or partial gene. As used herein, such wild type variant and its corresponding mutant variant are referred to as a "wild type—mutant variant pair". The skilled person will appreciate that a mutant sequence of a gene or a partial gene differs from the wild type sequence of said gene or partial gene by at least one nucleotide position.

Thus, in one embodiment, there is provided a device as disclosed herein, wherein the analysis section of the first sample analysis strip comprises at least one segment comprising at least a partial nucleic acid sequence of a wild type gene and the analysis section of the second sample analysis strip comprises at least one segment comprising the corresponding nucleic acid sequence of a mutant of said gene, which corresponding nucleic acid sequence encompasses at least one mutation. In one embodiment, said nucleic acid sequences are approximately 10-40 nucleotides long, such as 18-30 nucleotides long. In another embodiment, said nucleic acid sequences are approximately 60-130 nucleotides, such as 70-120 nucleotides long. In one embodiment, said nucleic acid sequence is biotinylated and/or attached with protein or peptide. In this context, the term "corresponding" refers to a nucleic acid sequence which comprises the mutation or multiple mutations whose presence or absence is to be detected. For example, the nucleic acid sequence of a mutant gene to its corresponding wild type gene comprises the variations of same or complementary nucleic acid sequences at 5' and/or 3' of the site of the mutation or mutations.

It is to be understood that said at least a partial nucleic acid sequence in said least one segment is coupled or conjugated or hybridised or immobilised to the analysis section, for example by covalent means or by hydrophobic means. Thus, in one embodiment of the device as disclosed herein, said at least partial nucleic acid sequence is covalently coupled to the at least one segment of the analysis section. In another embodiment of the device as disclosed herein, said at least partial nucleic acid sequence is coupled by hydrophobic or ionic or hydrogen bonding to the at least one segment of the analysis section.

The skilled person will appreciate that said at least partial nucleic acid sequence in said at least one segment of the analysis section may be attached by means of non-specific physical adsorption of a single-stranded DNA to a nitrocellulose, covalent attachment via diazo coupling, or by photochemical methods. For example, the nucleic acid to be attached may be heat-denatured and applied to the membrane in a salt buffer immobilized by UV irradiation (in the case of a nylon membrane) or baking (in the case of a nitrocellulose membrane) or modifying ionic interactions. The skilled person is aware of other suitable coupling means.

As used herein, the term "Lateral flow biosensors (LFNAB)" refer to sensors used in immunochromatographic test. The general principle is that test molecules in the reaction mixture flow by capillary movement mediated by gravitation and the visual signals (color change) are developed on the membrane strips by means of hybridization of substrates, such as for example streptavidin, biotin, horseradish peroxidase, conjugated gold nanoparticles (AuNP) or fluorophores. The skilled person will appreciate that many variants of said tests exist.

In one embodiment of the device, said analysis sections are formed of a transparent cellulose or polymer material. These materials favourable due to their sustainable character.

In one embodiment of the device, the backing film and the three-dimensional mark appearing in the segments have different colours in order to further improve the accuracy during the reading of the detected result and ensure that the information from the device is read correctly.

In one embodiment of the present disclosure, there is provided a device as disclosed herein, wherein the analysis section or strip comprises a membrane selected from the group consisting of nylon membrane, PVDF membrane, nitrocellulose membrane. In one particular embodiment, said membrane is a nitrocellulose membrane. In one embodiment, the analysis strip and the analysis section are of the same material.

It is to be understood that several different mutant—wild type variant pairs may be analyzed simultaneously on the same first and second sample analysis sections. For example, at least two different mutant—wild type variant pairs may be analyzed simultaneously on the same first and second sample analysis section, such at least 4, at least 6, at least 8 or at least 10. It is due to that each sample analysis section may contain several segments, wherein each segment comprises a nucleic acid sequence which either corresponds to the mutant or wild type sequence.

In one embodiment of the present disclosure, the sample pad and the part of the elongated sample analysis strips extending from the sample pad to the first segment is formed in one piece of material. This embodiment is very favourable since the sample will be able to flow faster, facilitating capillary forces, from the sample pad and through the sample analysis strips.

Thus, in one embodiment, there is provided a device wherein each sample analysis section contains at least 2 segments comprising different nucleic acids, such as at least 4 segments, such as at least 6 segments and such as at least 10 segments.

The present invention may be used for the detection of any Gram-positive or Gram-negative bacteria and their resistance markers. The present invention may also be used for the detection of for example pathogens causing diseases like actimomycsis, anthrax, Brucellosis, *Caphylobacter* infections, Cholera, Clostridial infections, diphtheria, diarrhea, enterococcal infections, erysipeothricosis, gas gangrene, enteric infections (due to *Klebsiella, Enterobactor, Serratia, Escheria coli*), Legionellosis, Leptospirosis, Lesteriosis, Lyme disease, meningococcal infections, pertussis, plague, Pneumonia, Pseudomonal infections, *Salmonellosis*, typhoid, meningococcal infections, Staphylococcal infections and cryptosporidial infections. Also markers for the above mentioned diseases may be detected, such as but not limited to methicillin resistance, extended spectrum beta-lactamase resistance, vancomycin resistance and metallo-resistance.

The present invention may also be useful for the identification of DNA and RNA viruses causing diseases animals and plants and their resistance markers, such as, but not limited to viruses that belong to the category of adeno, Epstein-Barr, Herpes, Hepatitis, Cytomegalovirus, influenza, HIV/AIDS, papilloma, polio, rabies, parainfluenza, respiratory syncytial, rubella and varicella-zoster.

The present invention may also be useful for the identification of fungal infections and their markers, such as, but not limited to, Aspergillosis, Blastomycosis, Candidiasis, Coccidioidomycosis (Valley Fever), *C. neoformans* infection, *C. gattii*, eye infections including Histoplasmosis, Mucormycosis, *Pneumocystis* pneumonia, worm infections like Ringworm, Round worm, Filariasis, Sporotrichosis and Ascaris.

As illustrated herein, the present device may be used in a genetic test for detection of pathogenic microbes and their resistance markers, including *Mycobacterium tuberculosis* complex. The *Mycobacterium tuberculosis* complex refers to a genetically related group of *Mycobacterium* species that can cause tuberculosis in humans, animals and other multicellular organisms. Non limiting examples of *Mycobacteria* species includes *Mycobacterium tuberculosis, Mycobacterium africanum, Mycobacterium bovis, Mycobacterium microti, Mycobacterium canetti, Mycobacterium caprae, Mycobacterium pinnipedii, Mycobacterium suricattae, Mycobacterium mungi, Mycobacterium avium, Mycobacterium intracellulare, Mycobacterium paratuberculosis*, and non-tuberculosis *mycobacterium* strains including *Mycobacterium leprae* and *Mycobacterium lepromatosis.*

In the Example section, the present invention is described in the context of a genetic test for detection antibiotic resistance markers in *Mycobacterium tuberculosis* complex. The skilled person will realize that this example in not to be viewed as limiting in any way. The device of the present disclosure is equally suitable in a genetic test for the indication of presence or absence of any nucleic acid with a predetermined sequence in a sample.

As used herein, the term "antibiotic resistance" refers to the presence of a mutation or mutations in the genes or modifications in proteins or enzymes in any living being which give rise to resistance to antimicrobials, including antibiotics. Such resistant phenotypes/genotypes do not respond to antibiotics.

As used herein, the term "antibiotic resistance marker" refers to the mutant variant of a gene, which variant confers the resistance to antimicrobials, including antibiotics.

In the context of the present disclosure a mutant-wild type variant pair may comprise an antibiotic resistance marker, which confers antibiotic resistance via mutation at any nucleotide position in genes, such as rpoB, katG, inhA, gyrA, rrs, eis or emb; and its wild type sequence, which does not confer antibiotic resistance. Non-limiting examples of antibiotic resistance markers of the *Mycobacterium tuberculosis* complex include rpoB 176 TGC, rpoB 432 GGC, rpoB 432 ACC, rpoB 432 AGC, rpoB 432 CAG, rpoB 432 CTG, rpoB 432 AGC, rpoB 432 CAG, rpoB 436 CTG, rpoB 437 AGC, rpoB 438 CAA, rpoB 438 TTC, rpoB 438 ATG, rpoB 441 GAC, rpoB 441 AAC, rpoB 441 CAG, rpoB 444 AAC, rpoB 444 CCG, rpoB 444 CTG, rpoB 447 TCG, rpoB 447 GGG, rpoB 447 TTG, rpoB 447 ACC, rpoB 451 CAC, rpoB 451 AAG, rpoB 451 CGC, rpoB 451 CGA, rpoB 451 CTG, rpoB 456 TCG, rpoB 456 GCG, rpoB 458 CTG, rpoB 486 CTG, rpoB 486 ATC, rpoB 496 CTG, rpoB 497 ATC, rpoB 513 CCA, rpoB 515 ATC, rpoB 516 TAC, rpoB 516 GTC, rpoB 522 TGG, rpoB 526 CGC, rpoB 526, rpoB 526 GAC, rpoB 526 CTC, rpoB 526 ACC, rpoB 531 TTG, rpoB 531 TGG, rpoB 533 CCG, rpoB 558 CGC, rpoB 598 GAG, katG 269 CGT, katG 463 CTG, katG 379 ACC, katG 98 TGC, katG 352 GAA, katG 463 CTG, katG 315 ACC, katG 202 GCA, katG 203 ACT, katG 518 GGTC insertion, katG 315 AAC, katG 127 CCG, katG 506 TAG, katG 315 ACA, katG 315 ACG, katG 315 ACT, katG 315 ATC, katG 315 AGA, katG 315 GGC, katG 315 CGC, inhA-15 T, inhA-8, inhA-17G, inhA-17T, inhA-34G, inhA-34T, mutations of inhA-47 T, ahpC-oxyR mutations at codons-10, -6, -39, -48, -15, 12 and -9, rrs 483 T, rrs 485 G, rrs 496A, rrs 491T, rrs 512T, rrs 798T, rrs 877A, rrs 904G, rrs 906 C, rrs 904 T, rrs 1401G, rpsL 43 AGG, rpsL 88 CAG, rpsL 128 G, rpsL 263 G, rpsL 262 C, gyrA 94G, gyrA 90T, gyrA 90V, gyrA S91P, gyrA D94A, gyrA D94G, gyrA 94N, gyrA 94H, emb 306v ATG, emb 306i ATG, eis-10G/A, eis-12C/T, eis-15 C/G, and rrs 1401 A/G. Non-limiting examples of corresponding wild type sequences include the conserved gene regions of katG wt, rpoB wt, gyrA wt, rrs wt, eis wt, emb wt, ahpC wt, oxyR wt, and rpsL wt, for example the gene sequences at the codons of rpoB 516 wt, katG 315 wt, rpoB 331 wt, rpoB 531 wt, rpoB 526 wt, inhA-15 wt, rrs 1401 wt, gyrA 94 wt, gyrA 90 wt, rpoB 533 wt, emb 306 wt, eis-10 wt, eis-12 wt, and eis-15 wt. In this context, an example of a mutant-wild type variant pair is rpoB 516 TAC and rpoB 516 wt.

In one embodiment there is provided a device as disclosed herein, wherein said gene comprises an antibiotic resistance marker, such as a *Mycobacterium tuberculosis* complex antibiotic resistance marker.

In one embodiment, said antibiotic resistance marker is selected from the group consisting of rpoB 176 TGC, rpoB 432 GGC, rpoB 432 ACC, rpoB 432 AGC, rpoB 432 CAG, rpoB 432 CTG, rpoB 432 AGC, rpoB 432 CAG, rpoB 436 CTG, rpoB 437 AGC, rpoB 438 CAA, rpoB 438 TTC, rpoB 438 ATG, rpoB 441 GAC, rpoB 441 AAC, rpoB 441 CAG, rpoB 444 AAC, rpoB 444 CCG, rpoB 444 CTG, rpoB 447 TCG, rpoB 447 GGG, rpoB 447 TTG, rpoB 447 ACC, rpoB 451 CAC, rpoB 451 AAG, rpoB 451 CGC, rpoB 451 CGA, rpoB 451 CTG, rpoB 456 TCG, rpoB 456 GCG, rpoB 458 CTG, rpoB 486 CTG, rpoB 486 ATC, rpoB 496 CTG, rpoB 497 ATC, rpoB 513 CCA, rpoB 515 ATC, rpoB 516 TAC, rpoB 516 GTC, rpoB 522 TGG, rpoB 526 CGC, rpoB 526, rpoB 526 GAC, rpoB 526 CTC, rpoB 526 ACC, rpoB 531 TTG, rpoB 531 TGG, rpoB 533 CCG, rpoB 558 CGC, rpoB 598 GAG, katG 269 CGT, katG 463 CTG, katG 379 ACC, katG 98 TGC, katG 352 GAA, katG 463 CTG, katG 315 ACC, katG 202 GCA, katG 203 ACT, katG 518 GGTC insertion, katG 315 AAC, katG 127 CCG, katG 506 TAG, katG 315 ACA, katG 315 ACG, katG 315 ACT, katG 315 ATC, katG 315 AGA, katG 315 GGC, katG 315 CGC, inhA-15 T, inhA-8, inhA-17G, inhA-17T, inhA-34G, inhA-34T, mutations of inhA-47 T, ahpC-oxyR mutations at codons-10, -6, -39, -48, -15, 12 and -9, rrs 483 T, rrs 485 G, rrs 496A, rrs 491T, rrs 512T, rrs 798T, rrs 877A, rrs 904G, rrs 906 C, rrs 904 T, rrs 1401G, rpsL 43 AGG, rpsL 88 CAG, rpsL 128 G, rpsL 263 G, rpsL 262 C, rrs 1401G, gyrA 94G, gyrA 90T, gyrA 90V, gyrA S91P, gyrA D94A, gyrA D94G, gyrA 94N, gyrA 94H, emb 306v ATG, emb 306i ATG, eis-10G/A, eis-12C/T, eis-15 C/G, and rrs 1401 A/G. In one embodiment, said antibiotic resistance marker is selected from the group consisting of rpoB 176 TGC, rpoB 432 GGC, rpoB 432 ACC, rpoB 432 AGC, rpoB 432 CAG, rpoB 432 CTG, rpoB 432 AGC, rpoB 432 CAG, rpoB 436 CTG, rpoB 437 AGC, rpoB 438 CAA, rpoB 438 TTC, rpoB 438 ATG, rpoB 441 GAC, rpoB 441 AAC, rpoB 441 CAG, rpoB 444 AAC, rpoB 444 CCG, rpoB 444 CTG, rpoB 447 TCG, rpoB 447 GGG, rpoB 447 TTG, rpoB 447 ACC, rpoB 451 CAC, rpoB 451 AAG, rpoB 451 CGC, rpoB 451 CGA, rpoB 451 CTG, rpoB 456 TCG, rpoB 456 GCG, rpoB 458 CTG, rpoB 486 CTG, rpoB 486 ATC, rpoB 496 CTG, rpoB 497 ATC, rpoB 513 CCA, rpoB 515 ATC, rpoB 516 TAC, rpoB 516 GTC, rpoB 522 TGG, rpoB 526 CGC, rpoB 526, rpoB 526 GAC, rpoB 526 CTC, rpoB 526 ACC, rpoB 531 TTG, rpoB 531 TGG, rpoB 533 CCG, rpoB 558 CGC and rpoB 598 GAG. In one embodiment, said antibiotic resistance marker is selected from the group consisting of katG 269 CGT, katG 463 CTG, katG 379 ACC, katG 98 TGC, katG 352 GAA, katG 463 CTG, katG 315 ACC, katG 202 GCA, katG 203 ACT, katG 518 GGTC insertion, katG 315 AAC, katG 127 CCG, katG 506 TAG, katG 315 ACA, katG 315 ACG, katG 315 ACT, katG 315 ATC, katG 315 AGA, katG 315 GGC, katG 315 CGC, inhA-15 T, inhA-8, inhA-17G, inhA-17T, inhA-34G, inhA-34T, mutations of inhA-47 T. In one embodiment, said antibiotic resistance marker is selected from the group consisting of, gyrA 94G, gyrA 90T, gyrA 90V, gyrA S91P, gyrA D94A, gyrA D94G, gyrA 94N, gyrA 94H, In one embodiment, said antibiotic resistance marker is selected from the group consisting of, ahpC-oxyR mutations at codons-10, -6, -39, -48, -15, 12 and -9, rrs 483 T, rrs 485 G, rrs 496A, rrs 491T, rrs 512T, rrs 798T, rrs 877A, rrs 904G, rrs 906 C, rrs 904 T, rrs 1401G, rpsL 43 AGG, rpsL 88 CAG, rpsL 128 G, rpsL 263 G, rpsL 262 C, rrs 1401G, gyrA 94G, gyrA 90T, gyrA 90V, gyrA S91P, gyrA D94A, gyrA D94G, gyrA 94N, gyrA 94H, emb 306v ATG, emb 306i ATG, eis-10G/A, eis-12C/T, eis-15 C/G, and rrs 1401 A/G.

In one embodiment of the device as disclosed herein, said at least one segment comprises a nucleic acid sequence of an antibiotic resistance marker selected from the group consisting of rpoB 176 TGC, rpoB 432 GGC, rpoB 432 ACC, rpoB 432 AGC, rpoB 432 CAG, rpoB 432 CTG, rpoB 432 AGC, rpoB 432 CAG, rpoB 436 CTG, rpoB 437 AGC, rpoB 438 CAA, rpoB 438 TTC, rpoB 438 ATG, rpoB 441 GAC, rpoB 441 AAC, rpoB 441 CAG, rpoB 444 AAC, rpoB 444 CCG, rpoB 444 CTG, rpoB 447 TCG, rpoB 447 GGG, rpoB 447 TTG, rpoB 447 ACC, rpoB 451 CAC, rpoB 451 AAG, rpoB 451 CGC, rpoB 451 CGA, rpoB 451 CTG, rpoB 456 TCG, rpoB 456 GCG, rpoB 458 CTG, rpoB 486 CTG, rpoB 486 ATC, rpoB 496 CTG, rpoB 497 ATC, rpoB 513 CCA, rpoB 515 ATC, rpoB 516 TAC, rpoB 516 GTC, rpoB 522 TGG, rpoB 526 CGC, rpoB 526, rpoB 526 GAC, rpoB 526 CTC, rpoB 526 ACC, rpoB 531 TTG, rpoB 531 TGG, rpoB 533 CCG, rpoB 558 CGC, rpoB 598 GAG, katG 269 CGT, katG 463 CTG, katG 379 ACC, katG 98 TGC, katG 352 GAA, katG 463 CTG, katG 315 ACC, katG 202 GCA, katG 203 ACT, katG 518 GGTC insertion, katG 315 AAC, katG 127 CCG, katG 506 TAG, katG 315 ACA, katG 315 ACG, katG 315 ACT, katG 315 ATC, katG 315 AGA, katG 315 GGC, katG 315 CGC, inhA-15 T, inhA-8, inhA-17G, inhA-17T, inhA-34G, inhA-34T, mutations of inhA-47 T, ahpC-oxyR mutations at codons-10, -6, -39, -48, -15, 12 and -9, rrs 483 T, rrs 485 G, rrs 496A, rrs 491T, rrs 512T, rrs 798T, rrs 877A, rrs 904G, rrs 906 C, rrs 904 T, rrs 1401G, rpsL 43 AGG, rpsL 88 CAG, rpsL 128 G, rpsL 263 G, rpsL 262 C, rrs 1401G, gyrA 94G, gyrA 90T, gyrA 90V, gyrA S91P, gyrA D94A, gyrA D94G, gyrA 94N, gyrA 94H, emb 306v ATG, emb 306i ATG, eis-10G/A, eis-12C/T, eis-15 C/G, and rrs 1401 A/G. In one embodiment, said at least one segment comprises a nucleic acid sequence of an antibiotic resistance marker selected from the group consisting of rpoB 176 TGC, rpoB 432 GGC, rpoB 432 ACC, rpoB 432 AGC, rpoB 432 CAG, rpoB 432 CTG, rpoB 432 AGC, rpoB 432 CAG, rpoB 436 CTG, rpoB 437 AGC, rpoB 438 CAA, rpoB 438 TTC, rpoB 438 ATG, rpoB 441 GAC, rpoB 441 AAC, rpoB 441 CAG, rpoB 444 AAC, rpoB 444 CCG, rpoB 444 CTG, rpoB 447 TCG, rpoB 447 GGG, rpoB 447 TTG, rpoB 447 ACC, rpoB 451 CAC, rpoB 451 AAG, rpoB 451 CGC, rpoB 451 CGA, rpoB 451 CTG, rpoB 456 TCG, rpoB 456 GCG, rpoB 458 CTG, rpoB 486 CTG, rpoB 486 ATC, rpoB 496 CTG, rpoB 497 ATC, rpoB 513 CCA, rpoB 515 ATC, rpoB 516 TAC, rpoB 516 GTC, rpoB 522 TGG, rpoB 526 CGC, rpoB 526, rpoB 526 GAC, rpoB 526 CTC, rpoB 526 ACC, rpoB 531 TTG, rpoB 531 TGG, rpoB 533 CCG, rpoB 558 CGC and rpoB 598 GAG. In one embodiment, said at least one segment comprises a nucleic acid sequence of an antibiotic resistance marker selected from the group consisting of katG 269 CGT, katG 463 CTG, katG 379 ACC, katG 98 TGC, katG 352 GAA, katG 463 CTG, katG 315 ACC, katG 202 GCA, katG 203 ACT, katG 518 GGTC insertion, katG 315 AAC, katG 127 CCG, katG 506 TAG, katG 315 ACA, katG 315 ACG, katG 315 ACT, katG 315 ATC, katG 315 AGA, katG 315 GGC, katG 315 CGC, inhA-15 T, inhA-8, inhA-17G, inhA-17T, inhA-34G, inhA-34T, mutations of inhA-47 T. I In one embodiment, said at least one segment comprises a nucleic acid sequence of an antibiotic resistance marker selected from the group consisting of, ahpC-oxyR mutations at codons-10, -6, -39, -48, -15, 12 and -9, rrs 1401G, gyrA 94G, gyrA 90T, gyrA 90V, gyrA S91P, gyrA D94A, gyrA D94G, gyrA 94N, gyrA 94H, emb 306v ATG, emb 306i ATG, eis-10G/A, eis-12C/T, eis-15 C/G, and rrs 1401 A/G.

In one embodiment, said at least one segment comprises a nucleic acid sequence of an antibiotic resistance marker selected from the group consisting of rpoB 513 CCA, rpoB 515 ATC, rpoB 516 TAC, rpoB 516 GTC, rpoB 522 TGG, rpoB 526 CGC, rpoB 526, rpoB 526 GAC, rpoB 526 CTC, rpoB 526 ACC, rpoB 531 TTG, rpoB 531 TGG and rpoB 533 CCG. For clarity reasons, this group is referred to below as antibiotic resistance marker of the X group. In one embodiment, said at least one segment comprises a nucleic acid sequence of an antibiotic resistance marker selected from the group consisting of katG 315 ACC, katG 202 GCA, katG 203 ACT, katG 518 GGTC insertion, katG 315 AAC, katG 127 CCG, katG 506 TAG, katG 315 ACA, katG 315 ACG, katG 315 ACT, katG 315 ATC, katG 315 AGA, katG 315 GGC, katG 315 CGC, inhA-15 T, inhA-8, inhA-17G and inhA-17T. For clarity reasons, this group is referred to below as antibiotic resistance marker of the Y group. In one embodiment, said at least one segment comprises a nucleic acid sequence of an antibiotic resistance marker selected from the group consisting of rpoB 516 TAC, rpoB 516 GTC, rpoB 526 CGC, rpoB 526, rpoB 526 GAC, rpoB 526 CTC, rpoB 526 ACC, rpoB 531 TTG, rpoB 531 TGG, rpoB 533 CCG, inhA-15 T, inhA-8, inhA-17G, inhA-17T, katG 315 ACC, katG 315 AAC, katG 315 ACA, katG 315 ACG, katG 315 ACT, katG 315 ATC, katG 315 AGA, katG 315 GGC and katG 315 CGC. For clarity reasons, this group is referred to below as antibiotic resistance marker of the Z group. In one embodiment, said at least one segment comprises a nucleic acid sequence of an antibiotic resistance marker selected from the group consisting of ahpC-oxyR mutations at codons-10, -6, -39, -48, -15, 12 and -9, rrs 1401G, gyrA 94G, gyrA 90T, gyrA 90V, gyrA S91P, gyrA D94A, gyrA D94G, gyrA 94N, gyrA 94H, emb 306v ATG, emb 306i ATG, eis-10G/A, eis-12C/T, eis-15 C/G, and rrs 1401 A/G. For clarity reasons, this group is referred to below as antibiotic resistance marker of the P group.

In one embodiment, said at least one segment of comprises a nucleic acid sequence of an antibiotic resistance marker selected from the group consisting of rpoB 531 TTG and katG 315 ACC. In one particular embodiment, said at least one segment of comprises a nucleic acid sequence selected from SEQ ID NO:2 and SEQ ID NO:4.

The skilled person will appreciate that an analysis section as disclosed herein may comprise a several segments, wherein each segment comprises a nucleic acid sequence of an antibiotic resistance marker which is different from the nucleic acid sequence in the other segments. Thus, the analysis section may comprise segments each comprising a nucleic acid sequence of a different antibiotic resistance marker. The skilled person will appreciate that the markers listed above may be freely combined in one or more analysis sections. For example, any analysis section may comprise a segment comprising any one of the listed antibiotic resistance marker in the X group above and a segment comprising any one of the listed antibiotic resistance marker in the Y group above. An analysis section may comprise a segment comprising a marker from the X group, a segment comprising a marker from the Y group, a segment comprising a marker from the Z group and a segment comprising a marker from the P group. It is also possible that an analysis section may comprise a segment comprising one or more markers from the one group and one or more segments comprising different markers from the same group. The skilled person will appreciate that the combinations listed here are not limiting.

Thus in one embodiment, said analysis section as disclosed herein comprises at least two segments, such as at least three segments, such as at least six segments, such as at least nine segments, such as least twelve segments, such as at least fourteen segments, which comprise nucleic acid sequence of different antibiotic resistance markers, such as different antibiotic resistance markers selected from different or the same groups listed above.

For example, an analysis section may comprise segments comprising a nucleic acid sequence of antibiotic resistance markers rpoB 176 TGC, rpoB 432 GGC, rpoB 438 CAA, rpoB 447 ACC, rpoB 516 TAC, rpoB 526 CGC, rpoB 531 TTG, katG 315 ACA, inha-15T, rrs 1401 G, gyrA 94G, emb 306v ATG and ies-10G/A, or a subset thereof. For example, an analysis section may comprise segments comprising a nucleic acid sequence of antibiotic resistance markers rpoB 432 ACC, rpoB 438 ATG, rpoB 447 GGG, rpoB 516 GTC, rpoB 526 GAC, rpoB 531 TGG, katG 315 ACT, inhA-8, gyrA 90T, emb 306i ATG and ies-12C/T, or a subset thereof. For example, an analysis section may comprise segments comprising a nucleic acid sequence of antibiotic resistance markers rpoB 432 CAG, rpoB 438 TTC, rpoB 447 TCG, rpoB 526 CTC, katG 315 GGC, inhA-17G and ies-15 C/G, or a subset thereof. For example, an analysis section may comprise segments comprising a nucleic acid sequence of antibiotic markers rrs 483 T, rrs 485 G, rrs 496A, rrs 491T, rrs 512T, rrs 798T, rrs 877A, rrs 904G, rrs 906 C, rrs 904 T, rrs 1401G, rpsL 43 AGG, rpsL 88 CAG, rpsL 128 G, rpsL 263 G and rpsL 262 C or a subset thereof. For example, an analysis section may comprise segments comprising a nucleic acid sequence of antibiotic resistance markers rpoB 432 CTG, rpoB 447 TTG, rpoB 526 ACC and katG 315 CGC or a subset thereof.

In one embodiment of the device as disclosed herein, said at least one segment comprising at least a partial nucleic acid sequence of a wild type gene comprises a sequence selected from, but non-limiting to, katG, rpoB, gyrA, rrs, eis, emb, ahpC, oxyR, at the codons of rpoB 516 wt, katG 315 wt, rpoB 331 wt, rpoB 531 wt, rpoB 526 wt, inhA-15 wt, rrs 1401 wt, gyrA 94 wt, gyrA 90 wt, rpoB 533 wt, emb 306 wt, eis-10 wt, eis-12 wt, and eis-15 wt. In this context, an example of a mutant-wild type variant pair is rpoB 516 TAC and rpoB 516 wt. In one embodiment, said at least one segment comprising at least a partial nucleic acid sequence of a wild type gene comprises a sequence selected from rpoB 531 wt and katG 315 wt. In one particular embodiment, said at least one segment comprises a sequence selected from SEQ ID NO:1 and SEQ ID NO:3.

It will be appreciated that the device as disclosed herein allows for analysis of the presence of absence of corresponding wild type sequences in the sample. For the sake of brevity, all such combinations of corresponding wild type sequences are not listed there. In one embodiment, all relevant wild type sequences are analyzed on one analysis section comprising several segments, wherein each segment comprises different wild type nucleic acid sequence. Thus, in one embodiment, an analysis section may comprise segments comprising a nucleic acid sequence of rpoB 176 wt, rpoB 432 wt, rpoB 438 wt, rpoB 447 wt, rpoB 516 wt, rpoB 526 wt, rpoB 531 wt, katG 315 wt, inhA-8, inhA-15, inhA-17 wt, 16s rRNA wt, gyrA 90, gyrA 91, gyrA 92, gyrA 93, gyrA 94, wt, emb 306 wt and ies-10, ies-12, eis-15 wt. rrs 483 wt, rrs 485 wt, rrs 496A wt, rrs 491 wt, rrs 512 wt, rrs 798 wt, rrs 877 wt, rrs 904 wt, rrs 906 wt, rrs 904 wt, rrs 1401 wt, rpsL 43 wt, rpsL 88 wt, rpsL 128 wt, rpsL 263 wt and rpsL 262 wt and ies-10, ies-12, eis-15 wt; In one embodiment, an analysis section may comprise segments comprising a nucleic acid sequences of rpoB 432 wt, rpoB 438 wt, rpoB 447 wt, rpoB 516 wt, rpoB 526 wt, rpoB 531 wt, katG 315 wt, inhA-8, inhA-15, inhA-17 wt, gyrA 90, gyrA 91T, gyrA 92T, gyrA 93G, gyrA 94, wt, emb 306 wt and ies-10, ies-12, eis-15 wt; or rpoB 432 wt, rpoB 438 wt, rpoB 447 wt, rpoB 526 wt, katG 315 wt, inhA-8 wt, inhA-15 wt, inhA-17 wt, rrs 483 wt, rrs 485 wt, rrs 496A wt, rrs 491 wt, rrs 512 wt, rrs 798 wt, rrs 877 wt, rrs 904 wt, rrs 906 wt, rrs 904 wt, rrs 1401 wt, rpsL 43 wt, rpsL 88 wt, rpsL 128 wt, rpsL 263 wt and rpsL 262 wt and ies-10, ies-12, eis-15 wt; or rpoB 432 wt, rpoB 447 wt, rpoB 526 wt and katG 315 wt.

It is also contemplated that the analysis section may comprise segments comprising a nucleic acid sequence of antibiotic resistance markers and a corresponding nucleic acid sequence of a wild type gene. For example, analysis section may comprise segments comprising a nucleic acid sequence of rpoB 176 wt and rpoB 176 TGC; rpoB 432 wt, rpoB 432 GGC, rpoB 432 ACC, rpoB 432 CAG and rpoB 432 CTG; rpoB 438 wt, rpoB 438 CAA, rpoB 438 ATG and rpoB 438 TTC; rpoB 447 wt, rpoB 447 ACC, rpoB 447 GGG, rpoB 447 TCG and rpoB 447 TTG; rpoB 516 wt, rpoB 516 TAC and rpoB 516 GTC; rpoB 526 wt, rpoB 526 CGC, rpoB 526 GAC, rpoB 526 CTC and rpoB 526 ACC; rpoB 531 wt, rpoB 531 TTG and rpoB 531 TGG; katG 315 wt, katG 315 ACA, katG 315 ACT, katG 315 GGC and katG 315 CGC; inhA-8 wt, inhA-15 wt, inhA-17 wt, inha-15T, inhA-8 and inhA-17G; 16s rRNAwt and rrs 1401 G; gyrA 90-94 wt gyrA 94G and gyrA 90T; emb 306 wt, emb 306v ATG, emb 306i ATG; or ies-8 wt, ies-12 wt, ies-15 wt, ies-10G/A, ies-12C/T and ies-15 C/G.

TABLE 1

| WT for analysis section 1 | Marker set for analysis section 2 | Marker set for analysis section 3 | Marker set for analysis section 4 | Marker set for analysis section 5 |
|---|---|---|---|---|
| rpoB 176 | rpoB 176 TGC | | | |
| rpoB 432 | rpoB 432 GGC | rpoB 432 ACC | rpoB 432 CAG | rpoB 432 CTG |
| rpoB 438 | rpoB 438 CAA | rpoB 438 ATG | rpoB 438 TTC | |

TABLE 1-continued

| WT for analysis section 1 | Marker set for analysis section 2 | Marker set for analysis section 3 | Marker set for analysis section 4 | Marker set for analysis section 5 |
|---|---|---|---|---|
| rpoB 447 | rpoB 447 ACC | rpoB 447 GGG | rpoB 447 TCG | rpoB 447 TTG |
| rpoB 516 | rpoB 516 TAC | rpoB 516 GTC | | |
| rpoB 526 | rpoB 526 CGC | rpoB526 GAC | rpoB 526 CTC | rpoB 526 ACC |
| rpoB 531 | rpoB 531 TTG | rpoB 531 TGG | | |
| katG 315 | katG 315 ACA | katG 315 ACT | katG 315 GGC | katG 315 CGC |
| inhA -8, inh -15, inhA -17 | inha-15T | inhA -8 | inhA -17G | |
| 16s rRNA | rrs 1401 G | | | |
| gyrA 90, gyrA 91, gyrA 92, gyrA 93, gyrA 94 | gyrA 94G | gyrA 90T | gyrA 91T | gyrA93G |
| emb 306 | emb 306v ATG | emb 306i ATG | | |
| Ies -10, ies -12, ies -15 | ies -10G/A | ies -12C/T | ies-15 C/G | |

It will be appreciated that in embodiments of the present device, wherein more than two analysis strips are present, said markers may be divided between said more than two strips.

As an example, it is envisioned that the device as disclosed herein comprises an analysis section for analysis of the wild type as illustrated in column 1 of Table 1 and at least one analysis section selected from sections illustrated in columns 2-5 in Table 1, such as column 1 and 2, column 1 and 3, column 1 and 4 and column 1 and 5. Also envisioned are combinations of an analysis section according to column 1 with columns 2 and 3; 2 and 4; 2 and 5, 3 and 4; 3 and 5; 4 and 5; 2, 3 and 4; 3, 4 and 5; 2, 4 and 5; 2, 3 and 5; or 2, 3, 4 and 5.

It is further contemplated that a sample analysis section may comprise at least a segment which enables detection of the bacterial species, such as one of the species included in the *Mycobacterium tuberculosis* complex. Additionally, the skilled person will appreciate that each sample analysis section may comprise a segment which acts as a control for any of the wild type and its mutation causing resistance in *Mycobacterium* species. In one particular embodiment, there is provided a device which comprises a sample analysis section comprising a control segment. In one embodiment, said control segment comprises at least a partial sequence of a house keeping gene of the bacterial species, such as a house keeping gene of *Mycobacterium tuberculosis* species and its resistance markers. In one particular embodiment, said sequence is SEQ ID NO:5.

In one embodiment of the device, the sample pad and elongated sample analyse strips are formed of absorbent fibre material through which the sample is able to flow by gravitational force or capillary movement. Other alternatives of materials are transparent cellulose materials or polymer materials.

The device is intended to be arranged for example on a table or desk such that the sample pad and elongated sample analysis strips are arranged substantially horizontal in order to facilitate the flow of the sample within the elongated sample analysis strips. Furthermore, the absorbent material used in the sample pad and analyse strips ensures that the sample is transferred to the sample analysis section.

One preferred embodiment of the device comprises a backing film made up of plastic or inert or opaque substance, arranged opposite to the inlet passage and the openings in the housing. The backing film prevents the liquid sample from leaking from the sample pad or sample analyse strip material before reaching the sample analysis section thereby improving the accuracy of the analysis result.

In one embodiment of the device, the elongated sample analysis strips first extend in substantially radial direction from the centre of the sample pad before they are angled such that the analysis sections are arranged parallel to each other and the result is detectable from the combination of segments arranged transverse to the elongated sample analysis strips. This embodiment is favourable since the sample easily can flow from the sample pad to the elongated sample strips which ensure that enough sample is transferred to each elongated sample analysis strip.

In one embodiment of the device, the corresponding segments of the first and second analysis section are arranged transverse to the analysis sections. This embodiment of the device makes it easy to read the correct analysis result in an easy and reliable way, for example, wild type and mutant genotypes. In one particular embodiment of the device, a detection agent is present in the sample analysis sections. In one embodiment, the detection agent is present in the segments of the analysis sections only.

One embodiment of the device, comprises a third elongated sample analysis strip configured to analyse different aspects of the nucleic acid sample, wherein the analysis section of said third sample strip is configured to analyse the presence or absence of nucleic acids with different predetermined sequences and have substantially the same length and is arranged between said first and second elongated sample analysis strip such that the analysis result is detectable from the combination of the corresponding segments of the three analysis strips. The third elongated sample analysis strip further increases the diagnostic accuracy of the analysis since further phenotypic variations could be detected.

In one embodiment of the device, an angle α within the range of 40°-80° is formed between the first and second elongated sample strip, and a notch, extending from the periphery towards the centre of the sample pad, is formed in the sample pad between the first and second elongated sample strip such that the sample is directed towards the first and second elongated sample strip. This design of the device ensures that the sample flows easily into the elongated sample analysis strips.

In one embodiment of the device, the third elongated sample strip extends in substantially radial direction from the sample pad from the tip of the notch.

One embodiment of the device, comprising a fourth and fifth elongated sample analysis strip configured to analyse different aspects of the nucleic acid sample, wherein the analysis section of said fourth and fifth sample strips are configured to analyse the presence or absence of nucleic acids with different predetermined sequences and have substantially the same length and is arranged on opposite sides of the first and second elongated sample analysis strip such that the analysis result is detectable from the combination of the corresponding segments of all four or five analysis strips. The fourth and fifth elongated sample analysis strip further increases the accuracy and provides details of the analysis since parameters like genus, species, housekeeping genes, wild type and resistance gene markers could be detected.

In one embodiment of the device, the fourth and fifth elongated sample strip extend in substantially radial direction from the centre of the sample pad before they are angled such that the analysis sections are arranged parallel to each other as well as the first and second analysis sections and aligned with the analysis sections of the first and second elongated sample strip.

One embodiment of the device comprises a support structure formed within the housing to support the sample pad and elongated sample strips in the correct position within the housing which is very important to ensure that the analysis result is displayed correctly.

In another aspect of the present disclosure there is provided a diagnostic method for determining the presence or absence of a target nucleic acid with a predetermined sequence in a sample from a subject, the method comprising the steps of:

a) providing a biological sample, which has previously been obtained from a subject in a non-invasive manner, b) subjecting the sample to selective amplification of at least one target nucleic acid with a predetermined sequence to obtain amplified target nucleic acid, c) applying the amplified target nucleic acid to the sample pad of the device (10; 30; 50) as described herein, d) incubating said device for a period sufficient to enable detection of said target nucleic acid by means of a detection agent, and e) detecting the presence or absence of the at least one target nucleic acid with a predetermined sequence.

In one embodiment of the method as disclosed herein, the said amplified target nucleic acid obtained in step b) is directly or indirectly coupled to a detection agent prior to applying the amplified target nucleic acid to the sample pad of the device.

In another embodiment, the amplified target nucleic acid obtained in step b) and the detection agent are separately added to the sample pad of the device, such that direct or indirect coupling occurs in situ. In one embodiment, said amplified target nucleic acid is added prior to the addition of the detection agent. In another embodiment, said detection agent is added prior to the addition of the amplified target nucleic acid.

In yet another embodiment, the detection agent is present in the sample pad and/or the analysis sections. In one embodiment, said detection agent is present in the segments of the analysis sections only. Hence, in this embodiment, the amplified target nucleic acid obtained in step b) in not coupled to a detection agent before it is added to the sample pad of the device as disclosed herein.

In one embodiment, said biological sample is obtained from said subject in a non-invasive manner, such as a non-surgical manner, which manner does not entail any risk to said patient and does not need to be performed by a medical professional. In one embodiment of the method as disclosed herein, the biological sample is a primary bacterial culture from said subject.

In one embodiment, said sample is a sample selected from biological fluids such as urine, blood, sputum and tissues, such as urine, blood and sputum, such as urine and sputum.

In one embodiment of the method as disclosed herein, the incubation in step e) is period sufficient to enable detection, which period is less than 180 minutes, such less than 120 minutes, such as less than 90 minutes, such as less than 80 minutes. It will be appreciated that the fast provision of analysis results is beneficial.

In one embodiment of the disclosed method, step c) is performed simultaneously with step b). In another embodiment, step c) is performed after step b).

In one embodiment of this method, the selective amplification in step b) is a multiplex selective amplification. A multiplex selective amplification refers to the simultaneous selective amplification of multiple different predetermined nucleic acid sequences in one reaction vial. Generally, target molecules may be amplified by a nucleic acid amplification method, such as isothermal amplification, however it remains a challenge to correctly identify point mutations in the target DNA, for example in case of drug resistant bacterial infections. Thus, the provision of a method which enables reliable and specific and selective amplification of target DNA is of crucial importance, which method allows accurate detection of single nucleotide variants.

Thus, in one embodiment of the second aspect of the present disclosure, there is provided a method, wherein the selective amplification in step b) is selected from the group consisting of polymerase chain reaction (PCR), reverse transcriptase PCR (RT-PCR), Branched DNA (quantiplex bDNA) tests, ligase chain reaction, transcription mediated amplification (TMA), Nucleic acid sequence-based amplification (NASBA), rolling circle amplification (RCA) in combination with target recognition by padlock probes (PLPs)

As an example, PLPs are linear oligonucleotide probes contain detection, restriction, specific tag and linker sequences, where the 5' and 3' arms (ends) are designed to hybridize to the target sequence. As the probe ends hybridize in juxtaposition on the target specific site, a perfect match at the 3' end is required for ligation, efficiently discriminating point mutations. The linker segment in the middle contains sequences with functions for amplification, identification and detection, even in a highly multiplexed fashion. The ligation-mediated circularized padlock can undergo RCA to produce a single-stranded concatemer, containing multiple complementary repeats of the PLP sequence. In order to improve the sensitivity, the concatemer may be restriction digested, re-ligated into new circles and subjected to an additional round of RCA, known as circle-to-circle amplification (C2CA). The restriction-digested amplicons (monomers) are hybridized in a sandwich fashion to their common tags of AuNP oligonucleotides and to the respective wild type and mutant oligonucleotide tags immobilized on the lateral flow strips to produce visual signals. Thus, in one embodiment of said method, the selective amplification in step b) is rolling circle amplification in combination with target recognition by padlock probes optionally comprising a circle-to-circle amplification step.

In one embodiment, said padlock probes are 70-120 nucleotides long, for example, 70 to 100 nucleotides long.

In one embodiment of the present method, the application step employs at least one padlock probe which is specific for an antibiotic resistance marker selected from the group consisting of rpoB 176 TGC, rpoB 432 GGC, rpoB 432 ACC, rpoB 432 AGC, rpoB 432 CAG, rpoB 432 CTG, rpoB 432 AGC, rpoB 432 CAG, rpoB 436 CTG, rpoB 437 AGC, rpoB 438 CAA, rpoB 438 TTC, rpoB 438 ATG, rpoB 441 GAC, rpoB 441 AAC, rpoB 441 CAG, rpoB 444 AAC, rpoB 444 CCG, rpoB 444 CTG, rpoB 447 TCG, rpoB 447 GGG, rpoB 447 TTG, rpoB 447 ACC, rpoB 451 CAC, rpoB 451 AAG, rpoB 451 CGC, rpoB 451 CGA, rpoB 451 CTG, rpoB 456 TCG, rpoB 456 GCG, rpoB 458 CTG, rpoB 486 CTG, rpoB 486 ATC, rpoB 496 CTG, rpoB 497 ATC, rpoB 513 CCA, rpoB 515 ATC, rpoB 516 TAC, rpoB 516 GTC, rpoB 522 TGG, rpoB 526 CGC, rpoB 526, rpoB 526 GAC, rpoB 526 CTC, rpoB 526 ACC, rpoB 531 TTG, rpoB 531 TGG, rpoB 533 CCG, rpoB 558 CGC, rpoB 598 GAG, katG 269 CGT, katG 463 CTG, katG 379 ACC, katG 98 TGC, katG 352 GAA, katG 463 CTG, katG 315 ACC, katG 202 GCA, katG 203 ACT, katG 518 GGTC insertion, katG 315 AAC, katG 127 CCG, katG 506 TAG, katG 315 ACA, katG 315 ACG, katG 315 ACT, katG 315 ATC, katG 315 AGA, katG 315 GGC, katG 315 CGC, inhA-15 T, inhA-8, inhA-17G, inhA-17T, inhA-34G, inhA-34T, mutations of inhA-47 T, ahpC-oxyR mutations at codons-10, -6, -39, -48, -15, 12 and -9, rrs 483 T, rrs 485 G, rrs 496A, rrs 491T, rrs 512T, rrs 798T, rrs 877A, rrs 904G, rrs 906 C, rrs 904 T, rrs 1401G, rpsL 43 AGG, rpsL 88 CAG, rpsL 128 G, rpsL 263 G and rpsL 262 C, rrs 1401G, gyrA 94G, gyrA 90T, gyrA 90V, gyrA S91P, gyrA D94A, gyrA D94G, gyrA 94N, gyrA 94H, emb 306v ATG, emb 306i ATG, eis-10G/A, eis-12C/T, eis-15 C/G, and rrs 1401 A/G. and at least one padlock probe which is padlock probe which is specific for the corresponding wild type sequence.

Non-limiting examples of corresponding wild type sequences include katG, rpoB, gyrA, rrs, eis, emb, ahpC, oxyR, at the codons of rpoB 516 wt, katG 315 wt, rpoB 331 wt, rpoB 531 wt, rpoB 526 wt, inhA-15 wt, rrs 1401 wt, gyrA 94 wt, gyrA 90 wt, rpoB 533 wt, emb 306 wt, eis-8 wt, eis-10 wt, eis-12 wt, eis-15 wt, rrs 483 wt, rrs 485 wt, rrs 496A wt, rrs 491 wt, rrs 512 wt, rrs 798 wt, rrs 877 wt, rrs 904 wt, rrs 906 wt, rrs 904 wt, rrs 1401 wt, rpsL 43 wt, rpsL 88 wt, rpsL 128 wt, rpsL 263 wt and rpsL 262 wt. In this context, an example of a mutant-wild type variant pair is rpoB 516 TAC and rpoB 516 wt.

In one embodiment of the present method, the application step employs at least padlock probes which are specific for the antibiotic resistance markers rpoB 513 CCA, rpoB 515 ATC, rpoB 516 TAC, rpoB 516 GTC, rpoB 522 TGG, rpoB 526 CGC, rpoB 526, rpoB 526 GAC, rpoB 526 CTC, rpoB 526 ACC, rpoB 531 TTG, rpoB 531 TGG and rpoB 533 CCG, and padlock probes which is specific for the corresponding wild type sequence. In one embodiment of the present method, the application step employs at least padlock probes which are specific for the antibiotic resistance markers katG 315 ACC, katG 202 GCA, katG 203 ACT, katG 518 GGTC insertion, katG 315 AAC, katG 127 CCG, katG 506 TAG, katG 315 ACA, katG 315 ACG, katG 315 ACT, katG 315 ATC, katG 315 AGA, katG 315 GGC, katG 315 CGC, inhA-15 T, inhA-8, inhA-17G and inhA-17T, and padlock probes which is specific for the corresponding wild type sequence. In one embodiment of the present method, the application step employs at least padlock probes which are specific for the antibiotic resistance markers rpoB 516 TAC, rpoB 516 GTC, rpoB 526 CGC, rpoB 526, rpoB 526 GAC, rpoB 526 CTC, rpoB 526 ACC, rpoB 531 TTG, rpoB 531 TGG, rpoB 533 CCG, inhA-15 T, inhA-8, inhA-17G, inhA-17T, katG 315 ACC, katG 315 AAC, katG 315 ACA, katG 315 ACG, katG 315 ACT, katG 315 ATC, katG 315 AGA, katG 315 GGC and katG 315 CGC, and padlock probes which is specific for the corresponding wild type sequence.

In one embodiment of the present method, the application step employs at least padlock probes which are specific for the antibiotic resistance markers ahpC-oxyR mutations at codons-10, -6, -39, -48, -15, 12 and -9, rrs 1401G, gyrA 94G, gyrA 90T, gyrA 90V, gyrA S91P, gyrA D94A, gyrA D94G, gyrA 94N, gyrA 94H, emb 306v ATG, emb 306i ATG, eis-10G/A, eis-12C/T, eis-15 C/G, and rrs 1401 A/G, and padlock probes which is specific for the corresponding wild type sequence. In one embodiment of the present method, the application step employs at least padlock probes which are specific for the antibiotic resistance markers rpoB 176 TGC, rpoB 432 GGC, rpoB 438 CAA, rpoB 447 ACC, rpoB 516 TAC, rpoB 526 CGC, rpoB 531 TTG, katG 315 ACA, inha-15T, rrs 1401 G, gyrA 94G, emb 306v ATG and ies-10G/A and padlock probes which is specific for the corresponding wild type sequence. In one embodiment of the present method, the application step employs at least padlock probes which are specific for the antibiotic resistance markers rpoB 432 ACC, rpoB 438 ATG, rpoB 447 GGG, rpoB 516 GTC, rpoB 526 GAC, rpoB 531 TGG, katG 315 ACT, inhA-8, gyrA 90T, emb 306i ATG and ies-12C/T and padlock probes which is specific for the corresponding wild type sequence. In another embodiment of the present method, the application step employs at least padlock probes which are specific for the antibiotic resistance markers rpoB 432 CAG, rpoB 438 TTC, rpoB 447 TCG, rpoB 526 CTC, katG 315 GGC, inhA-17G and ies-15 C/G and padlock probes which is specific for the corresponding wild type sequence. In yet another embodiment of the present method, the application step employs at least padlock probes which are specific for the antibiotic resistance markers rpoB 432 CTG, rpoB 447 TTG, rpoB 526 ACC and katG 315 CGC and padlock probes which is specific for the corresponding wild type sequence. In another embodiment of the present method, the employment of resistance markers rrs 483 wt, rrs 485 wt, rrs 496A wt, rrs 491 wt, rrs 512 wt, rrs 798 wt, rrs 877 wt, rrs 904 wt, rrs 906 wt, rrs 904 wt, rrs 1401 wt, rpsL 43 wt, rpsL 88 wt, rpsL 128 wt, rpsL 263 wt and rpsL 262 wt and ies-10, ies-12, eis-15 wt and the mutant codons of The skilled person will appreciate that the combination of padlock probes employed is dependent the identity of the antibiotic resistance markers which absence of presence is to be detected and that any combination of markers listed in relation to the first aspect of the present invention is equally relevant for this second aspect. For the sake of brevity, the listings are not repeated here.

In one example, the padlock probes used in the selective amplification in step b) may be specific for the antibiotic resistance markers rpoB 516 TAC, rpoB 516 GTC and for the corresponding wt sequence rpoB 516 wt, respectively. In another example, the padlock probes used in the selective amplification in step b) may be specific for the antibiotic resistance markers rpoB 531 TGG and rpoB 531 wt, respectively. In one embodiment, said padlock probes comprise the sequence SEQ ID NO:10 and SEQ ID NO:9, respectively. In yet another example, the padlock probes used in the selective amplification in step b) may be specific for the antibiotic resistance markers katG 315 ACC and katG 315 wt, respectively. In one embodiment, said padlock probes comprise the sequence SEQ ID NO:8 and SEQ ID NO:7, respectively. The skilled person will appreciate that several different padlock probes may be combined in one selective amplification, for example one selective amplification reaction may be carried out using several padlock probes each specific for one of rpoB 531 TGG, rpoB 531 wt, katG 315 ACC and katG 315 wt. In a particular embodiment of the method as disclosed herein, the padlocks probes are at least one of SEQ ID NO:7-10, such as at least two of SEQ ID NO:7-10, such as at least three SEQ ID NO:7-10, such as all four of SEQ ID NO:7-10. In one embodiment, said padlocks probes are SEQ ID NO:7 and 8. In another embodiment, said padlock probes are SEQ ID NO:9 and 10.

Requirement of sophisticated instruments, such as fluorometers, fluorescence microscopes, array scanners in order to read RCA or C2CA signals hamper the use of RCA in resource-limited laboratories, such as peripheral laboratory settings, and calls for alternative methods. The skilled person will appreciate that the present device may be used as a method which does not require advanced and expensive analysis equipment and hence is suitable for peripheral laboratories.

In embodiments of present method, the amplified target nucleic acid molecule is coupled to a detection agent. Such coupling may be direct or indirect coupling, for example via means on an additional nucleic acid molecule. Methods of coupling a detection molecule to a nucleic acid molecule are well established in the art and the skilled person is aware of suitable methods, including electrical or mechanical or ionic or chemical or in combination of these methods. Non-limiting examples of organic and inorganic nucleic acid detection agents and their combination include radionuclides, gold nanoparticles, fluorophores or any colored substances, aptamers or linkers, streptavidin-associated agents, biotin, horseradish peroxidase, or conjugated gold nanoparticles (AuNP). In one embodiment, said detection agent are gold nanoparticles, such a gold nanoparticles conjugated to a nucleic acid molecule. In some embodiment said detection agent is visually detectable. In some embodiments, said detection agent provides a color signal.

In a related aspect there is provided a kit comprising a device as described herein and at least one probe specific for a multi-resistance marker, at least one probe which is specific for the corresponding wild type sequence, and a detection agent as disclosed herein. For example, the padlock probes combinations thereof as described may be used. The skilled person will appreciate that the description of the resistance markers and padlock probes in relation to the first and second aspects of the present disclosure are equally relevant for this third aspect.

Thus as shown in Example 1 of the present disclosure, the nucleic acid amplification may involve combinatorial usage and integration of padlock probes, rolling circle amplification, lateral flow read-out device and gold nanoparticles to provide visible signals of view for simplified evaluation of the test result, as discussed in detail below. For example lateral flow test strip may have nucleic acid conjugated oligonucleotides with or with out gold nanoparticles as an integral part and a method for the preparation of said test strip for the detection and/or determination of a nucleic acid. Nucleic acid conjugated gold nanoparticles are stabilized in dry form and retain all their properties after rehydration (shape, texture, mobility, hybridization capacity and colloidal state). The presence of the target nucleic acid in the sample is detected by the formation of two red bands on the test and control zones.

While the invention has been described with reference to various exemplary aspects and embodiments, it will be understood by those skilled in the art that various changes may be made and equivalents may be substituted for elements thereof without departing from the scope of the invention. In addition, many modifications may be made to adapt a particular situation or molecule to the teachings of the invention without departing from the essential scope thereof. Therefore, it is intended that the invention not be limited to any particular embodiment contemplated, but that the invention will include all embodiments falling within the scope of the appended claims.

BRIEF DESCRIPTION OF THE FIGURES

FIG. 4 is a listing of the nucleic acid sequences of disclosed in Example 1 with SEQ ID NO:1-18.

Figure 5A:
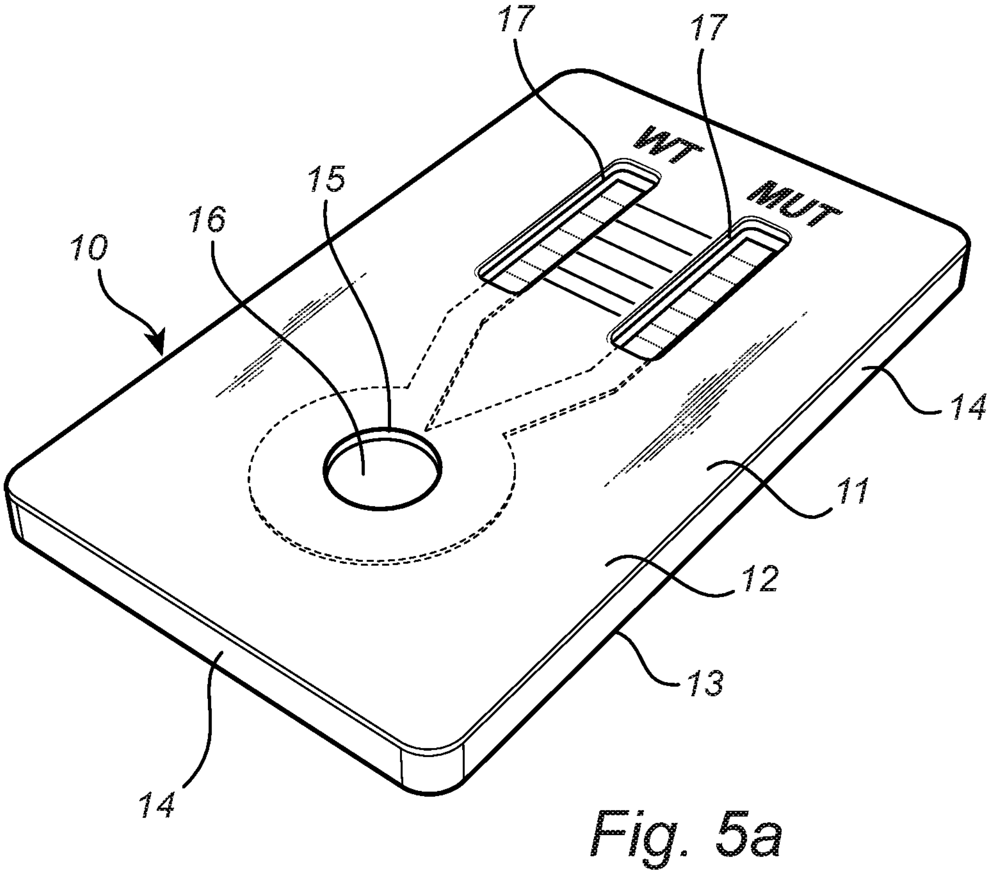
FIGS. 5*a*, 6*a* and 7*a* illustrates a perspective view of different embodiments of the device 10; 30; 50 according to the invention. The devices 10; 30; 50 are intended for analysing liquid samples comprising amplified nucleic acids.

The device 10 illustrated in FIG. 5*a* comprises a rectangular protective housing 11 that has a front side 12, back side 13 and four side surfaces 14. The device 10 is intended to be arranged substantially horizontal with the front side 12 facing upwards during use.

In the front side 12 of the housing 11, a substantially circular sample inlet passage 15 is formed such that the sample that needs to be analysed could access a sample pad 16 from the outside of the housing 11. Furthermore, two openings 17 through which the analysis result could be viewed are formed in the front side of the housing. The openings 17 could be covered by a transparent layer to protect the interior of the housing. The size and shape of the sample inlet passage 15 and the openings 17 could be modified in several ways without departing from the scope of the invention. For example, the two openings could be replaced by one larger opening.

The housing is for example made of a plastic material that provides support for the different components of the device and provides the required protection to the device.

Figure 5B:
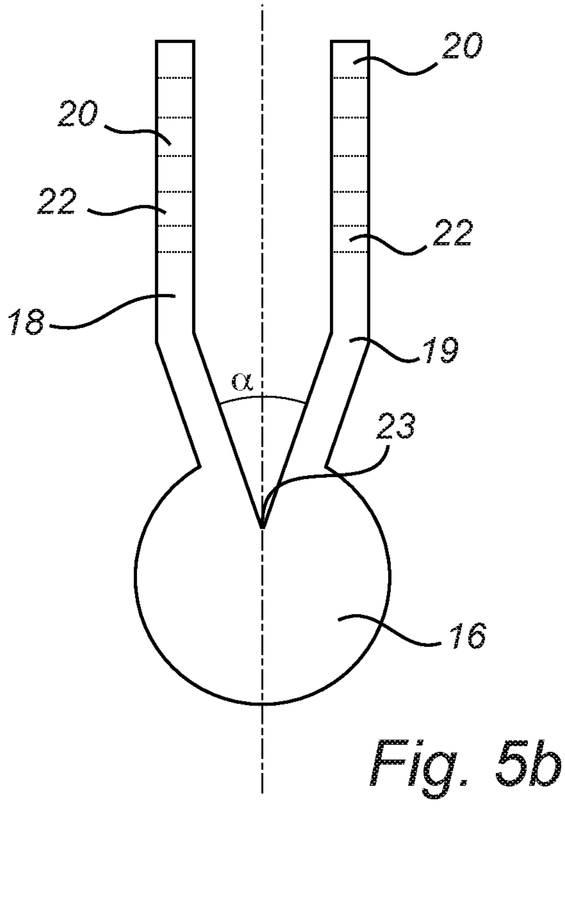
FIGS. 5*b* and 8 illustrate schematically a sample pad and a first and a second elongated analysis strip of an embodiment 10 of the device.

The housing encloses a sample pad 16 and a first 18 and second 19 elongated sample analysis strips illustrated schematically in FIG. 5*b*.

Figure 8:
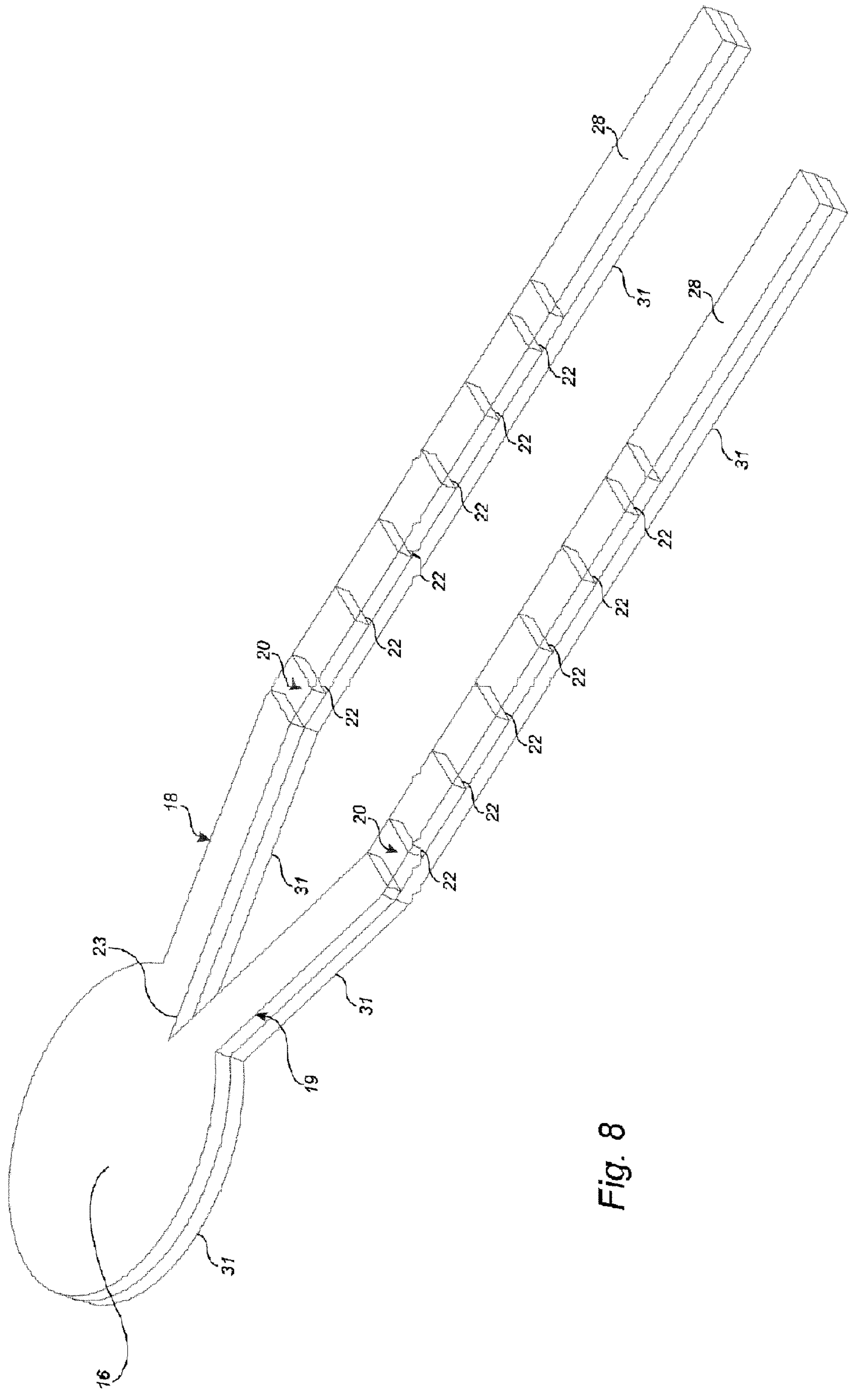

The sample pad 16 is in the illustrated embodiments substantially circular and made of an absorbent fibre material for example made of glass, synthetic fibres or a cellulose material. The liquid sample is supplied to the sample pad 16 and flowing through the sample pad by capillary movement to the first 18 and second 19 elongated sample analysis strips. This embodiment is illustrated in FIG. 5*b* and FIG. 8.

In order to facilitate the flow of the sample, a notch 23 extending from the periphery of the sample pad towards the centre of the sample pad is formed in the sample pad between the first and second elongated analysis strip. The illustrated sample pad is substantially circular but the shape could be modified in several ways to facilitate the flow of the sample to the elongated sample analysis strips. An alternative shape could be like a droplet with the narrow end facing the elongated sample analysis strips.

The first section of the sample analysis strips, connected to the sample pad 16, is preferably made of the same material as the sample pad 16 to transfer the sample to the respective sample analysis section 20. In order to further improve the transfer of the sample from the sample pad to the sample analyse strips, the sample pad and the part of the elongated sample analysis strips extending from the sample pad to the sample analysis section is formed in one piece of material.

The analysis sections 20 of the first and second elongated sample strips have the same length and are arranged parallel to each other side by side such that the result is readable from the front side of the housing from the combined result from the two sample analysis sections 20 of each strip.

Each analysis section comprises the same number of segments 22. The segments 22 in each sample analyse section are arranged side by side to provide the desired contact between adjacent segments and make it possible for the sample to flow through the sample analysis section. The sample analysis section, i.e. the different segments arranged adjacent to each other, are made of a transparent material arranged above the backing film 31. The transparent material has a thickness of at least 0.1 mm and once one of the segments is detecting the predetermined gene or substance in the sample, a three-dimensional mark appears within the transparent layer of the segment. The transparent layer in combination with the backing film provides a very distinct mark that is easy for the user to read. The different segments are not visible on the analysis strips but when the sample is applied, a mark will appear in the segment corresponding to the result from the analysed sample. The result is detectable by the combination of the two corresponding transverse segments of the first and second sample analysis stripe.

An angle $\alpha$ within the range of 40°-80° is formed between the first and second elongated sample strip to ensure that the sample flows easily into the elongated sample analysis strips.

Figure 6A:
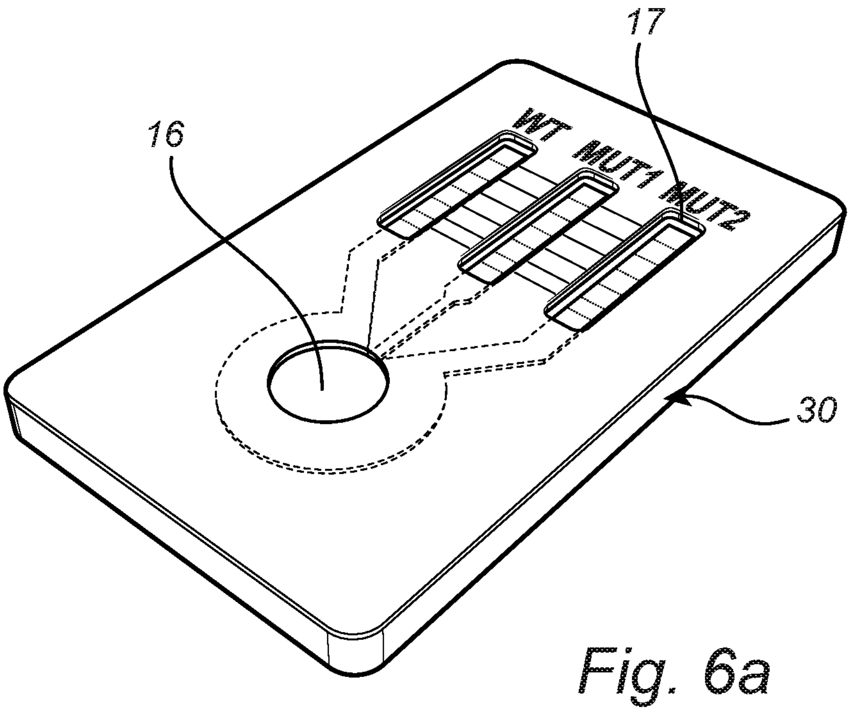
Figure 6B:
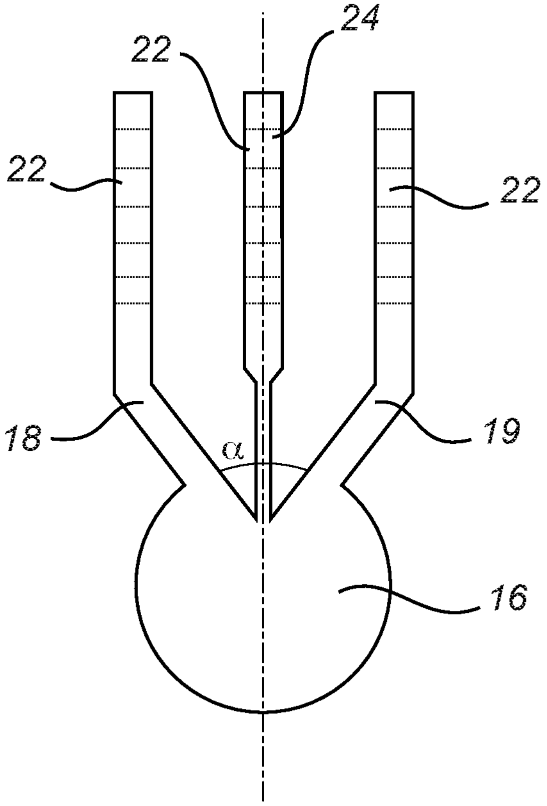
FIG. 6*b* illustrates schematically a sample pad and a first, a second and a third elongated analysis strip of an embodiment 30 of the device.

In FIGS. 6*a* and 6*b* an alternative embodiment of the device is illustrated schematically. The housing has substantially the same design as in the previous embodiment but the device comprises an additional third elongated sample analysis strip arranged between the first and second elongated sample analysis strip. The third elongated sample analysis strip is substantially identical to the first and second elongated sample analysis strip and makes it possible to analyse further characteristics in the same device. The third elongated sample strip extend in substantially radial direction from the centre of the sample pad from the tip of the notch formed between the first and second elongated sample analysis strip.

Figure 7A:
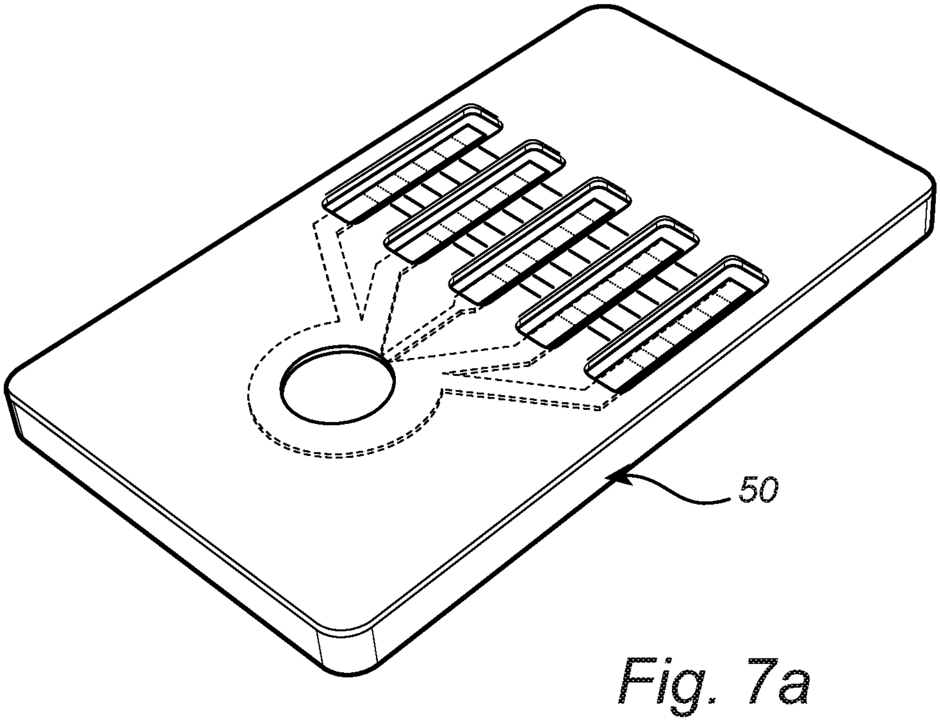
Figure 7B:
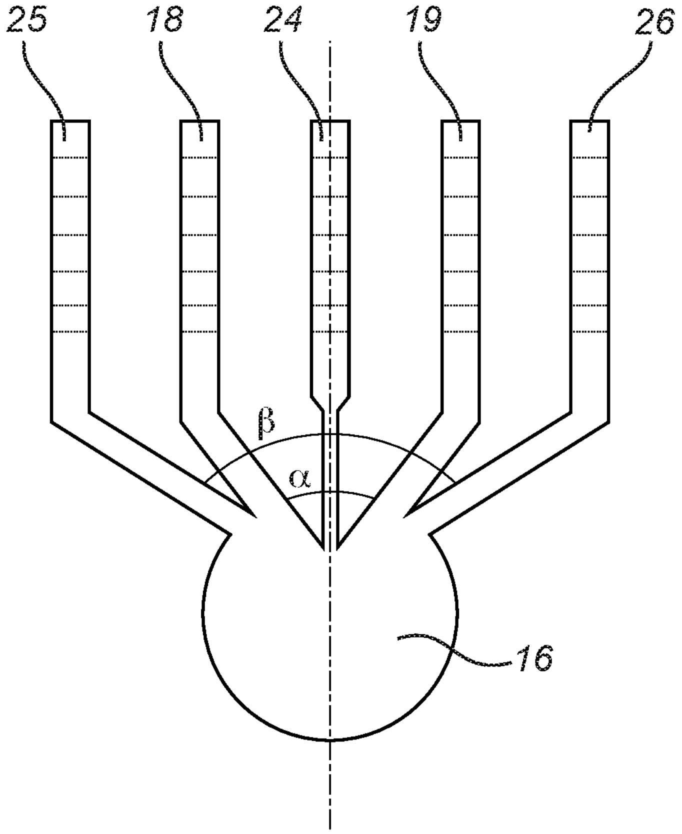
FIG. 7*b* illustrates schematically a sample pad and a first, a second, a third, a fourth and a fifth elongated analysis strip of an embodiment 50 of the device.

In FIGS. 7*a* and 7*b* a further alternative embodiment 50 of the device 30 is illustrated schematically. The housing has substantially the same design as in the previous embodiment but the device comprises a fourth 25 and a fifth 26 elongated sample analysis strip arranged on outside the first and second elongated sample analysis strip, i.e. on opposite sides of the first and second elongated sample analysis strip. The fourth and fifth elongated sample analysis strips are substantially identical to the first and second elongated sample analysis strip and makes it possible to analyse further characteristics in the same device. The fourth and fifth elongated sample strip first extend in substantially radial direction from the centre of the sample pad before they are angled such that the sample sections are arranged parallel and side by side to the sample sections of the first and second elongated sample analysis section.

An angle β within the range of 60°-100° is formed between the fourth and fifth elongated sample strip to ensure that the sample is flowing easily into all elongated sample analysis strips.

In FIG. 7*b* sample section is illustrated in perspective. The sample pad 16 and elongated sample analysis strips 18, 19, 24, 25, 26 preferably comprises a plastic backing film 31 arranged opposite to the inlet passage 15 and the openings 17 in the housing to prevent that the liquid sample is leaking from the sample pad and elongated sample analysis strips. Each of the first, second, third, fourth and fifth elongated sample analysis strip comprises a analysis section 20 comprising a number of segments prepared to display a mark if a predetermined nucleic acid sequences are detected in the liquid sample flowing through the sample section 20. Each of the first, second, third, fourth and fifth elongated sample analysis strip furthermore comprises an absorbent pad 28 arranged in the end of the sample strip. The absorbent pad facilitates the flow of sample through the analysis section 20.

The different segments 22 of the sample sections 20 are not visible before the sample has been applied and the result is displayed on the sample analysis section by a line or symbol that are appearing on the sample analysis strip if the particular bacteria or nucleic acid is triggering the marking on that segment is detected in the sample.

The number of segments in the sample section 20 could be adapted to the specific analysis that the device is adapted for but mostly comprises at least 5 segments. The analysis result is read from the combination of the result indicated on the respective sample analysis sections arranged side by side, i.e. the two, three or five segments arranged transverse to the sample sections 20.

EXAMPLE 1

Summary

The following Examples disclose proof of concept the preparation and analysis of samples *Mycobacterium tuberculosis* complex (MTB) underlying the present invention.

Materials and Methods

Chemicals and Oligonucleotides:

Streptavidin from *Streptomyces avidinii*, gold(III)chloride trihydrate (HAuCl4), sucrose, dithiothreitol (DTT), Triton X-100, trisodium citrate, Tris (hydroxymethyl)aminomethane hydrochloride (Tris-HCl), Tween 20, Ethylenediaminetetraacetic acid (EDTA) and bovine serum albumin (BSA, for oligonucleotide-AuNP conjugates), Sodium chloride-sodium citrate (SSC) buffer (pH 7.0), phosphate buffer saline (PBS, pH 7.4, 0.01 M), and sodium chloride (NaCl, 5 M, pH 7.0), ATP, dNTPs, oligonucleotides (purchased from Integrated DNA Technologies and Sigma-Aldrich). For the LF assay, binder-free borosilicate glass fiber pads (grade A/C), cellulose fiber absorbent pads (grade 113) and nitrocellulose membrane attached to the laminated cards/strips (0.4 and 0.5 cm width).

Bacterial Strains and DNA Extraction:

The reference strain MTB H37Rv (ATCC 25618) and ten clinical MTB isolates (Table 2) were cultured on Lowenstein-Jensen medium with and without 40 mg/L of RIF, respectively. DNA was extracted and 10 μg of genomic DNA was fragmented enzymatically using 10 U each of Nael and HpyCH4V, and 1× CutSmart buffer (New England Biolabs, Ipswich, Mass., USA) at 37° C. for 90 min followed by enzyme inactivation at 65° C. for 20 min. DNA concentration was measured by the dsDNA HS and BR assays using Qubit 2.0 fluorometer (Life Technologies, Carlsbad, Calif., USA).

TABLE 2

Genotypic information on strains.

| Strain ID | rpoB genotype | katG genotype |
|---|---|---|
| 2 | S531L (TCG/TTG) | S315T (AGC/ACC) |
| 4 | S531L (TCG/TTG) | S315T (AGC/ACC) |
| 8 | S531L (TCG/TTG) | S315T (AGC/ACC) |
| 9 | S531L (TCG/TTG) | S315T (AGC/ACC) |
| 12 | S531L (TCG/TTG) | S315T (AGC/ACC) |
| 13 | S531L (TCG/TTG) | WT |
| 17 | S531L (TCG/TTG) | S315T (AGC/ACC) |
| 19 | WT | WT |
| 20 | WT | WT |
| 21 | WT | WT |

Padlock Probes and Rolling Circle Amplification:

Sequences of oligonucleotides used in this study are given in FIG. 4. Four PLPs were designed to target two codons in the genes katG and rpoB and their corresponding wild type sequences (katG 315 ACC (MUT), katG 315 AGC (WT), rpoB 531 TTG (MUT) and rpoB 531 TCG (WT). After verifying secondary structures using Mfold Web Server, the PLPs were phosphorylated at the 5' end by incubating a reaction mixture consisting of 1 μM oligonucleotide, 1×PNK buffer A, 1 mM ATP), and 1 U/μl T4 polynucleotide kinase (Thermo Scientific, Waltham, Mass., USA) at 37° C. for 30 min, followed by enzyme inactivation at 65° C. for 20 min. Confirmation of PLP efficacy was done by performing C2CA [Dahl et al. *Proc Natl Acad Sci USA* 2004, 101, 4548-4553] with modifications. Sensitivity of the assay was evaluated by LF strips with amplicons prepared from 300 pg, 3 ng, 30 ng and 300 ng of genomic DNA.

Preparation and Characterization of Oligonucleotide Conjugated Gold Nanoparticles:

Gold nanoparticles were prepared by a standard citrate reduction method [Frens G. *Nature Phys Sci.* 1973, 241, 20-22] with modifications. In a dry 500 mL round-bottom borosilicate glass flask, cleaned in aquaregia (nitric acid and hydrochloric acid in 3:1 ratio), 100 mL of 0.01% HAuCl4 in MilliQ water was boiled with vigorous stirring. Four milliliters of 1% trisodium citrate solution was added and after turning wine-red. Fifty micromolar of thiolated oligonucleotide, designed to hybridize to a sequence present in all C2CA monomers, was reduced by 500 mM of DTT in SSC buffer for 30 min. A NAP™-5 column (GE Healthcare Biosciences, Little Chalfont, UK) was used to purify the oligonucleotides and eluted directly into 1 mL of AuNPs. After incubating it for 2 h at 37° C., 1 M NaCl was incrementally added and kept for 'aging' at 4° C. The solution was centrifuged at 13,000 g for 25 min, the supernatant discarded and the AuNP-oligonucleotide conjugates re-dispersed in 1 mL of 5% BSA, 0.25% Tween 20 and 20 mM Tris-HCl (pH 8.0).

Conventional transmission electron microscope (TEM) images of the prepared AuNP were obtained at 100 kV to check the quality of the prepared particles. The AuNP-oligonucleotide conjugates were characterized by measuring their light absorption at 520 nm in a Multi-Mode Microplate Reader (SpectraMaxR M5, Molecular Devices) and their surface charge (ζ-potential) was measured by dynamic light scattering (DLS) using Zetasizer Nano ZS90 (Malvern, UK) equipped with a 4.0 mW HeNe laser and an avalanche photodiode detector.

Design, Assembly and Preparation of Lateral Flow Strips:

The 100×5 mm LF strip consists of a sample application pad, nitrocellulose membrane and absorbent pad that are mounted on a thin plastic backing. The dry sample pad (25×5 mm), after saturation with 1% BSA, 1% Triton X-100, 20 mM Tris-HCl, 100 mM NaCl; pH 8.0), fixed on one end of the nitrocellulose membrane (45×5 mm) with an overlap of 2-3 mm and the absorbent pad (30×5 mm) was fixed on the other end of the nitrocellulose membrane. The biotinylated strip oligonucleotides (FIG. 3) were immobilized in test and control zones on the nitrocellulose membrane. The control zone contained one line of immobilized oligonucleotides complementary to the AuNP-oligonucleotide conjugates. The test zone contained 4 lines separated by 3 mm, where each line consisted of unique strip oligonucleotides for detection of the C2CA monomers corresponding to their specific genotypes of katG 315 WT, katG 315 MUT (AGC/ACC), rpoB 531 WT and rpoB 531 MUT (TCG/TTG) by hybridization. Fifty micromolar of the strip oligonucleotide was mixed with an equal volume of 1×PBS containing 15 μM of streptavidin. After incubation at 37° C. for 2 h, the streptavidin-conjugated oligonucleotide was immobilized on the nitrocellulose membrane using a nanoplotter (Nano-Plotter NP2.0, GeSiM, Grosserkmannsdorf, Germany).

Visualization of C2CA Amplicons on Lateral Flow Strips:

Fifty-five microliters of the C2CA monomers (amplified nucleic acid fragments) were hybridized with 13 μL of AuNP-oligonucleotide conjugates and applied to the sample pad of LF strips, drop by drop. The sample was allowed to flow for 5-7 min and washed with 4×SSC buffer for visualization of the red color bands. Color development in the control line indicated the positive assay control, while the signals from each test line specifically referred to presence of WT and/or MUT genotypes of katG 315 and rpoB 531. Intensity graphs were generated for the bands and pixel-densities were measured to quantify the results in densitograms, using the open source tool ImageJ (Version 1.49q) [Schneider et al. Nat. Meth. 2012, 9, 671-675]

Results

As shown herein, the present Example provides a proof-of-principle assay which able to produce rapid visual signals to discriminate between wild type and the mutations in katG and rpoB genes, causing MDR-TB, i.e. resistance to INH and RIF. The method can produce visual signals in approximately 75 min and the results can guide clinicians in taking informed decisions on public health control actions as well as adjusting to an effective antibiotic regimen. This assay provides preliminary alternative information to the time-consuming conventional DST and offers a compatible solution for resource-limited clinical laboratories. Thus, there present inventors have developed a simple, specific and cost-effective diagnostic test for the prompt identification of drug and/or antibiotic resistance. The DNA-based test is suitable for application in resource-limited clinical laboratories and provides information about the drug and/or antibiotic resistance pattern of bacteria infecting a patient, which is valuable for clinicians in order to take appropriate actions for treatment and infection control.

Figure 1:
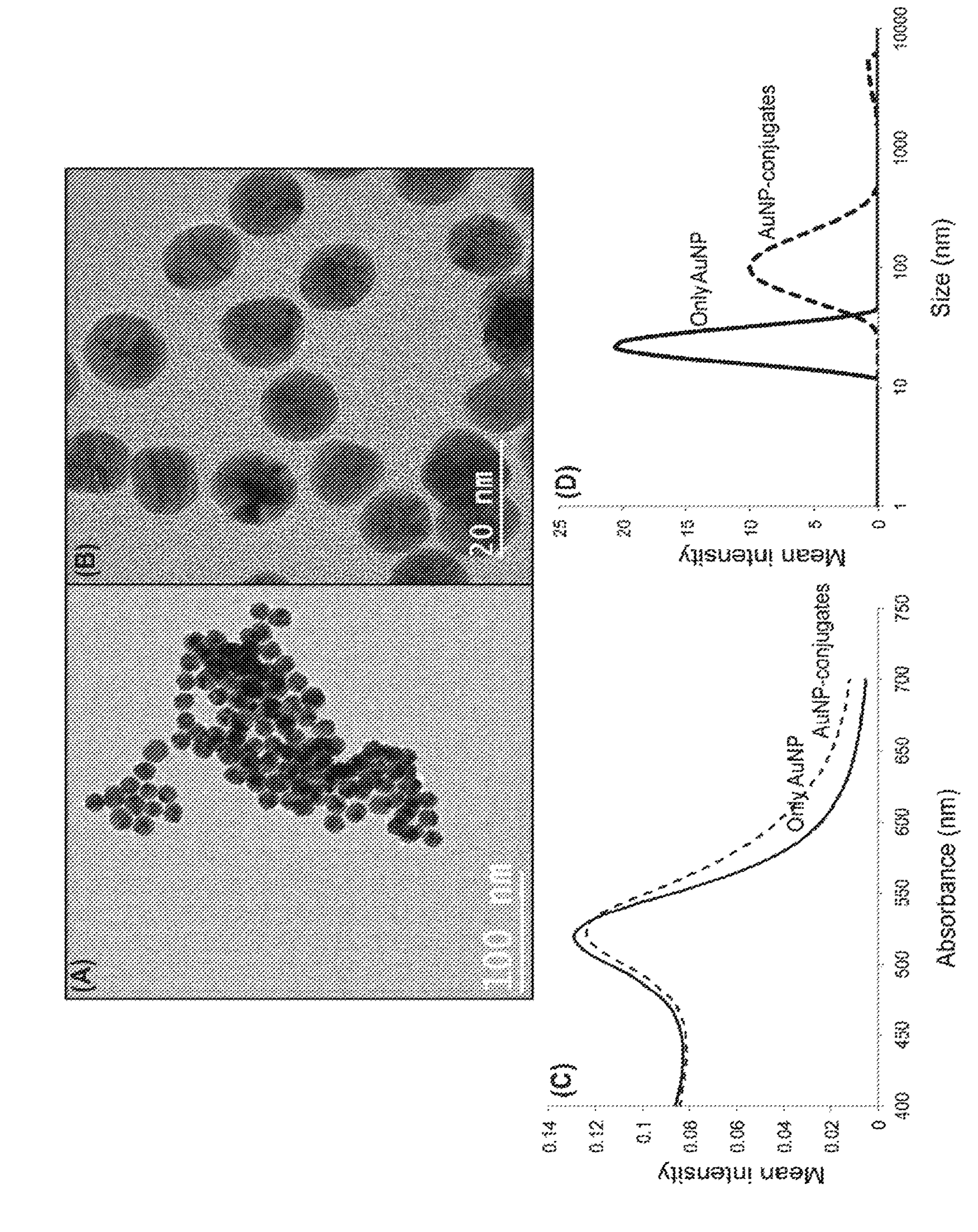
FIG. 1 shows transmission electron microscopic (TEM) images at 50,000× and 300,000× magnification (A and B) shows that the gold nanospheres have an average diameter of 15±0.5 nm. A shift light absorbance spectra (C) from 520 nm to 528 nm shows that the prepared gold particles are conjugated with the oligonucleotides. Single smooth spectrum of DLS measurements (D) confirms conjugation and monodispersion of the AuNP-oligonucleotide conjugates.

Evaluation of AuNP-Oligonucleotide Conjugates:

The TEM images of the AuNP (FIGS. 1 A and B) confirm the size of sphered particles to be ±3.5 nm. Size distribution curve based on the light absorption of AuNP showed a λ-max at 520 nm before oligonucleotide conjugation and the peak shifted to 527 nm after the conjugation (FIG. 1C). The DLS measurements (FIG. 1D) revealed an average diameter of 90±4 nm with a single peak indicating monodispersed solution without particle aggregation. The ζ-potential measurements of −37.4 mV and −34.5 mV for AuNP and their oligonucleotide-conjugates, respectively, showed that the preparations were stable.

Figure 2:
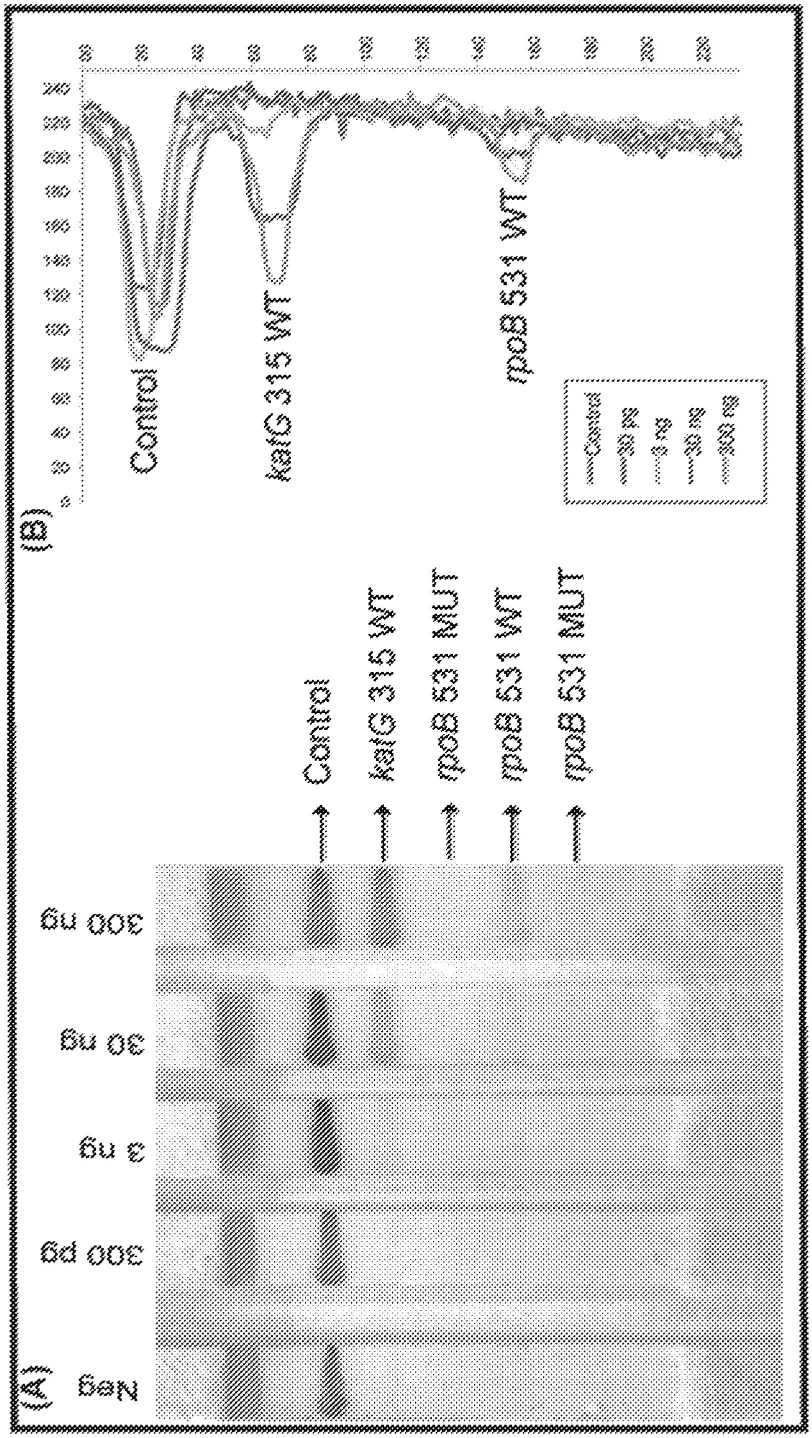
FIG. 2 shows the results from the investigation of the limit of detection of the PLP-LF method by testing 10-fold dilutions of genomic MTB DNA (A). The densitograms in B, plotted by computing the local color intensities, depicts the semi-quantitative changes in the control and test lines.

Limit of Detection of Padlock Probe-Lateral Flow Test:

Limit of detection (LOD) of this PLP-LF assay was performed in triplicates by testing various dilutions of genomic DNA from the reference strain MTB H37Rv. Since both signals were clearly observed with 300 ng of DNA (FIG. 2A), in this proof-of-concept study, further experiments with DNA from clinical samples (Table 2) were performed using this amount. Densitograms (FIG. 2B) based on the local pixel density of red color signals developed on lateral flow strips correlated with the visual observation. The signal intensity of rpoB 531 WT was lower compared to katG 315 WT, which could be due to the high GC content in the target region of the rpoB gene, potentially resulting in a lower yield of C2CA monomers. Minor variations were observed among the densitograms of control lines, even though the lateral flow strips from the same printing session were used. The improvements to achieve higher sensitivity would enable direct testing on sputum samples.

Figure 3:
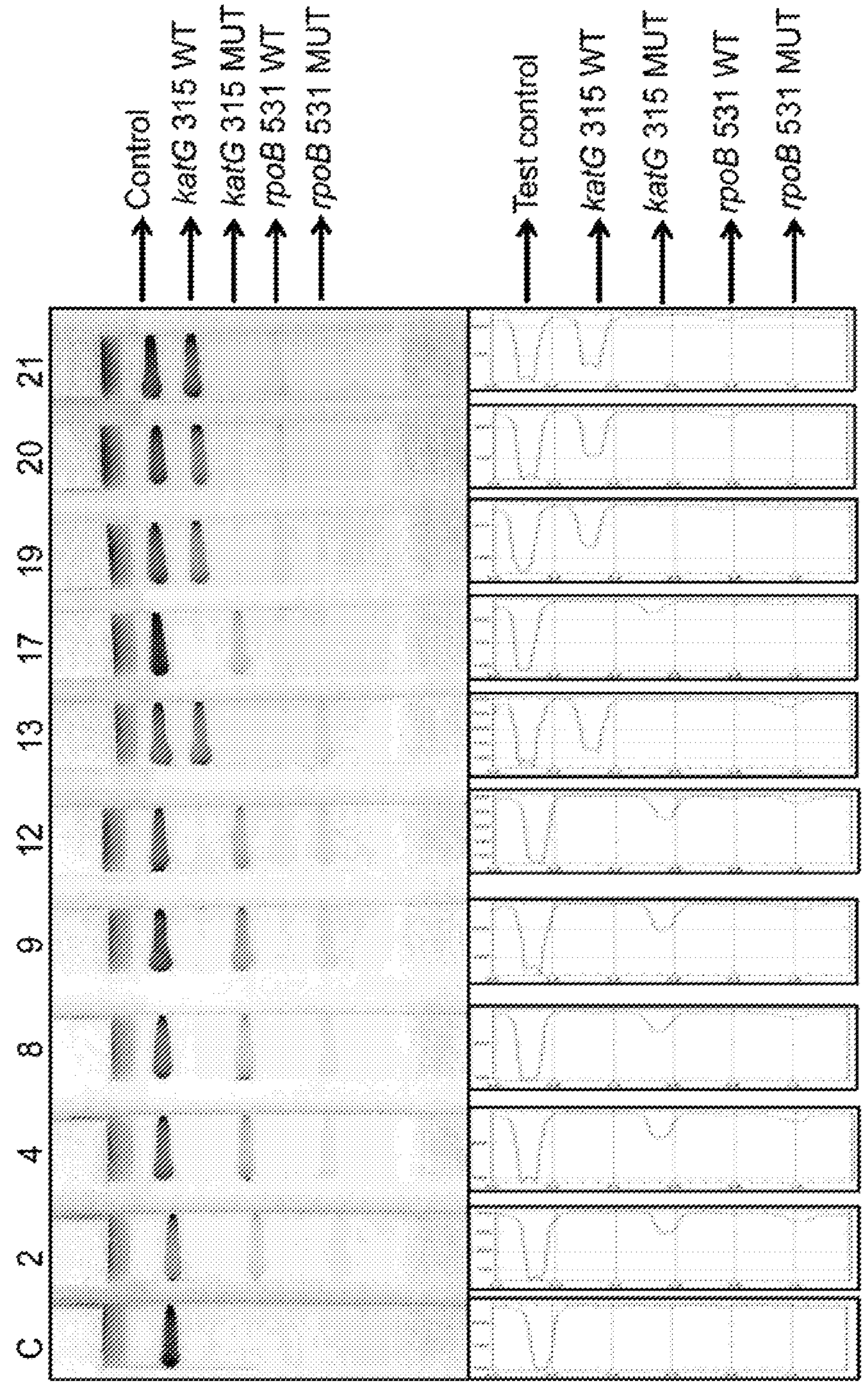
FIG. 3 shows the results from testing characterized genomic DNA samples (300 ng) isolated from clinical MTB containing wild type or mutant codons of rpoB 531 and katG 315. The densitograms qualitatively shows the presence and/or absence of wild type and/or mutant genotypes of the clinical isolates.

Visual Evaluation of the Padlock Probe-Lateral Flow Test on Clinical Isolates of MTB:

A set of 10 clinical isolates MTB (Table 2) that were resistant and/or susceptible to INH and RIF, were tested by the PLP-LF method. As seen in FIG. 3, six strains (ID numbers: 2, 4, 8, 9, and 12) contained a mutant katG and rpoB codons; three strains (19, 20 and 21) possessed only wild type codons and one strain (13) showed the presence of wild type katG codon but mutant rpoB codon. All the visual signals of PLP-LF assay of the tested strains were fully concordant to genotypic characterization of the strains by pyrosequencing and the respective densitograms below each LF strip correspond to their visual signals. The method could be expanded by including a variety of other mutations causing MDR-TB, and the sensitivity could be improved for application directly on sputum samples from TB patients.

The invention claimed is:

1. A device (10; 30; 50) for analysing a liquid sample comprising amplified nucleic acids, said device comprising:

a sample pad (16);

a first sample analysis strip (18) and a second sample analysis strip (19), wherein the first and second strips are elongated and extend from the sample pad and each of said first and second strips comprises a straight analysis section (20) divided into multiple segments (22), each segment of said first or second analysis strip having immobilized thereto nucleic acids which sequence is different to a nucleic acid sequence of any other segment of said first or second analysis strip and that is complementary to a target nucleic acid sequence, wherein said segments are configured to indicate the presence or absence of a target nucleic acid sequence in said liquid sample, and wherein the analysis sections of said first and second sample analysis strips comprises a backing film covered by a transparent layer, wherein said transparent layer has a thickness of at least 0.1 mm, said analysis sections of the first and second sample analysis strips having the same length and being arranged side by side such that the analysis result is detectable from the combination of three-dimensional marks appearing in the transparent layer of aligned segments of said first and second analysis strips, and a housing (11) enclosing said sample pad and at least two elongated sample analysis strips, said housing comprising a front side (12) in which a sample inlet passage (15) is formed such that the sample pad is accessible from the outside of the housing and at least one opening (17) such that the analysis result is detectable from the outside of the housing, wherein the sample pad and the sample analysis strips are formed from a material that extends from the sample pad through the analysis strips, said material comprising a single continuous piece of backing film and a single continuous transparent layer, wherein said transparent layer is on top of the backing film.

2. The device according to claim 1, wherein the analysis section of the first sample analysis strip comprises at least one segment comprising at least a partial nucleic acid sequence of a wild type gene and the analysis section of the second sample analysis strip comprises at least one segment comprising the corresponding nucleic acid sequence of a mutant of said gene, which corresponding nucleic acid sequence encompasses at least one mutation.

3. The device according to claim 2, wherein said gene comprises at least one antibiotic resistance marker, such as a *Mycobacterium tuberculosis* antibiotic resistance marker.

4. The device according to claim 3, wherein said at least one antibiotic resistance marker is selected from the group consisting of rpoB 516 TAC, rpoB 516 GTC, katG 315 ACC, rpoB 531 TTG, rpoB 531 TGG, rpoB 526 TAC, rpoB 526 GAC, rpoB 526 CTC, rpoB 526 ACC, inhA-15 T, rrs 1401 G, gyrA 94 GGC, gyrA 90 GTG and rpoB 533 CCG.

5. The device according to claim 1, wherein said analysis sections are lateral flow biosensors.

6. The device according to claim 1, wherein said analysis sections are formed of a transparent cellulose or polymer material.

7. The device according to claim 1, wherein the backing film (31) and the three-dimensional mark appearing in the segments have different colours.

8. The device according to claim 1, wherein the first and second elongated sample strips first extend in a radial direction from the centre of the sample pad before they are angled such that the analysis sections of the first and second elongated sample analysis strips are arranged parallel to each other and the result is detectable from the combination of segments arranged transverse to the elongated sample analysis strips.

9. The device according to claim 1, wherein the corresponding segments of the first and second analysis section are arranged transverse to the analysis sections.

10. The device according to claim 1, further comprising a third sample analysis strip (24), wherein the third sample analysis strip is elongated and extends from the sample pad between said first and second elongated sample analysis strips, and wherein the third sample analysis strip comprises a straight analysis section divided into multiple segments, each segment of said analysis strip having immobilized thereto nucleic acids which sequence is different to a nucleic acid sequence of any other segment of said first, second or third analysis strip and that is complementary to a target nucleic acid sequence, wherein said segments are configured to indicate the presence or absence of a target nucleic acid in the liquid sample, and said analysis section of said third sample analysis strip having the same length and is arranged between said first and second elongated sample analysis strips such that the analysis result is detectable from the combination of the corresponding segments of the three analysis strips.

11. The device according to claim 8, wherein an angle α within the range of 40°-80° is formed between the first and second elongated sample strip, and a notch (23), extending from the periphery towards the centre of the sample pad, is formed in the sample pad between the first and second elongated sample strip such that the sample is directed towards the first and second elongated sample strip.

12. The device according to claim 10, wherein the third elongated sample strip extends in a radial direction from the sample pad from the tip of the notch.

13. The device according to claim 1, further comprising a fourth (25) and fifth (26) sample analysis strips, wherein the fourth and fifth sample analysis strips are elongated and extends from the sample pad, and wherein the fourth and fifth analysis strips comprises a straight analysis section divided into multiple segments, each segment of said analysis strip having immobilized thereto nucleic acids which sequence is different to a nucleic acid sequence of any other segment of said first, second, third, fourth or fifth analysis strip and that is complementary to a target nucleic acid sequence, wherein said segments are configured to indicate the presence or absence of a target nucleic acid sequence in the liquid sample, and said analysis section of said fourth and fifth sample strips having the same length and are arranged on opposite sides of the first and second elongated sample analysis strip such that the analysis result is detectable from the combination of the corresponding segments of all four or five analysis strips.

14. The device according to claim 10, wherein the fourth and fifth elongated sample strip extend in a radial direction from the centre of the sample pad before they are angled such that the analysis sections are arranged parallel to each other as well as the first and second analysis sections and aligned with the analysis sections of the first and second elongated sample strip.

15. The device according to claim 1, wherein a support structure is formed within the housing to support the sample pad and elongated sample strips in the correct position within the housing.

16. A method for determining the presence or absence of a target nucleic acid sequence in a sample from a subject, the method comprising the steps of:

a) providing a biological sample, which has previously been obtained from a subject in a non-invasive manner, b) subjecting the sample to selective amplification of at least one target nucleic acid with a predetermined sequence to obtain amplified target nucleic acid, c) applying the amplified target nucleic acid to the sample pad of the device (10; 30; 50) according to claim 1, d) incubating said device for a period sufficient to enable detection of said target nucleic acid by means of a detection agent, and e) detecting the presence or absence of the at least one target nucleic acid with a predetermined sequence.

17. The method according to claim 16, wherein said nucleic acid is DNA or RNA, such as bacterial DNA, such as DNA from *Mycobacterium tuberculosis* complex.

18. A kit comprising a device according to claim 1 and at least one probe specific for a multi-resistance marker, at least one probe which is specific for the corresponding wild type sequence, and a detection agent.

* * * * *